US010813637B2

(12) United States Patent
Shelton, IV et al.

(10) Patent No.: US 10,813,637 B2
(45) Date of Patent: Oct. 27, 2020

(54) THREE DIMENSIONAL ADJUNCTS

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US); Chester O. Baxter, III, Loveland, OH (US)

(73) Assignee: Ethicon LLC, Guaynabo, PR (US)

( * ) Notice: Subject to any disclaimer, the term of this patent is extended or adjusted under 35 U.S.C. 154(b) by 250 days.

(21) Appl. No.: 15/901,713

(22) Filed: Feb. 21, 2018

(65) Prior Publication Data

US 2019/0254657 A1 Aug. 22, 2019

(51) Int. Cl.
| | |
|---|---|
| *A61B 17/064* | (2006.01) |
| *A61B 17/072* | (2006.01) |
| *A61L 31/06* | (2006.01) |
| *A61L 31/14* | (2006.01) |
| *B33Y 80/00* | (2015.01) |

(Continued)

(52) U.S. Cl.
CPC .... *A61B 17/0644* (2013.01); *A61B 17/07207* (2013.01); *A61B 17/07292* (2013.01); *A61L 31/04* (2013.01); *A61L 31/041* (2013.01); *A61L 31/06* (2013.01); *A61L 31/146* (2013.01); *A61L 31/148* (2013.01); *A61L 31/16* (2013.01); *B29C 64/153* (2017.08); *B33Y 10/00* (2014.12); *B33Y 70/00* (2014.12); *B33Y 80/00* (2014.12); *A61B 2017/00004* (2013.01); *A61B 2017/00526* (2013.01); *A61B 2017/00862* (2013.01); *A61B 2017/00889* (2013.01); *A61B 2017/00893* (2013.01); *A61B 2017/00964* (2013.01); *A61B 2017/07257* (2013.01); *A61B 2017/07271* (2013.01); *A61B 2017/07278* (2013.01); *A61B 2017/07285* (2013.01); *A61L 2300/404* (2013.01); *B29K 2995/006* (2013.01); *B29K 2995/0056* (2013.01); *B29L 2031/7546* (2013.01)

(58) Field of Classification Search
None
See application file for complete search history.

(56) References Cited

U.S. PATENT DOCUMENTS

| | | | |
|---|---|---|---|
| D297,764 | S | 9/1988 | Hunt et al. |
| 4,892,244 | A | 1/1990 | Fox et al. |

(Continued)

FOREIGN PATENT DOCUMENTS

| | | |
|---|---|---|
| EP | 0449431 A2 | 10/1991 |
| EP | 594148 A1 | 4/1994 |

(Continued)

OTHER PUBLICATIONS

International Search Report and Written Opinion for PCTIB2019050402 dated Apr. 30, 2019 (6 pages).

(Continued)

*Primary Examiner* — Hemant Desai
*Assistant Examiner* — Tanzim Imam
(74) *Attorney, Agent, or Firm* — Mintz Levin Cohn Ferris Glovsky and Popeo, P.C.

(57) ABSTRACT

Stapling assemblies for use with a surgical stapler and methods for manufacturing the same are provided. Three dimensional adjuncts for use with a surgical stapling assembly and methods for manufacturing the same are also provided.

20 Claims, 21 Drawing Sheets

(51) Int. Cl.
  *B33Y 10/00* (2015.01)
  *B29C 64/153* (2017.01)
  *A61L 31/16* (2006.01)
  *A61L 31/04* (2006.01)
  *B33Y 70/00* (2020.01)
  *A61B 17/00* (2006.01)
  *B29L 31/00* (2006.01)

(56) References Cited

U.S. PATENT DOCUMENTS

| | | |
|---|---|---|
| RE34,519 E | 1/1994 | Fox et al. |
| 7,195,640 B2 | 3/2007 | Falotico et al. |
| 7,641,091 B2 | 1/2010 | Olson et al. |
| 8,590,762 B2 | 11/2013 | Hess et al. |
| 9,211,120 B2 * | 12/2015 | Scheib ............... A61B 17/068 |
| 9,307,965 B2 | 4/2016 | Ming et al. |
| 9,332,984 B2 | 5/2016 | Weaner et al. |
| 9,924,944 B2 | 3/2018 | Shelton, IV et al. |
| 10,028,744 B2 | 7/2018 | Shelton, IV et al. |
| 10,052,104 B2 | 8/2018 | Shelton, IV et al. |
| D831,209 S | 10/2018 | Huitema et al. |
| D836,198 S | 12/2018 | Harris et al. |
| 10,166,026 B2 | 1/2019 | Shelton, IV et al. |
| 10,172,616 B2 | 1/2019 | Murray et al. |
| 10,271,849 B2 | 4/2019 | Vendely et al. |
| 10,335,150 B2 | 7/2019 | Shelton, IV |
| D882,782 S | 4/2020 | Shelton, IV et al. |
| 2009/0090763 A1 | 4/2009 | Zemlok et al. |
| 2012/0080344 A1 | 4/2012 | Shelton, IV |
| 2012/0241491 A1 | 9/2012 | Aldridge et al. |
| 2012/0241497 A1 | 9/2012 | Mandakolathur Vasudevan et al. |
| 2012/0241502 A1 * | 9/2012 | Aldridge ............ A61B 17/1155 227/176.1 |
| 2012/0241505 A1 | 9/2012 | Alexander, III et al. |
| 2012/0253298 A1 | 10/2012 | Henderson et al. |
| 2012/0318842 A1 | 12/2012 | Anim et al. |
| 2013/0161374 A1 * | 6/2013 | Swayze ............... A61B 17/105 227/176.1 |
| 2013/0161375 A1 | 6/2013 | Huitema et al. |
| 2013/0253661 A1 | 9/2013 | D'Agostino et al. |
| 2013/0256375 A1 | 10/2013 | Shelton, IV et al. |
| 2013/0317526 A1 | 11/2013 | Mortarino |
| 2014/0155916 A1 * | 6/2014 | Hodgkinson .... A61B 17/07292 606/151 |
| 2014/0224857 A1 | 8/2014 | Schmid |
| 2015/0034696 A1 | 2/2015 | Shelton, IV et al. |
| 2015/0133995 A1 | 5/2015 | Shelton, IV et al. |
| 2015/0297222 A1 | 10/2015 | Huitema et al. |
| 2015/0313594 A1 | 11/2015 | Shelton, IV et al. |
| 2015/0351754 A1 | 12/2015 | Harris et al. |
| 2015/0351758 A1 * | 12/2015 | Shelton, IV ..... A61B 17/00491 606/219 |
| 2015/0351858 A9 | 12/2015 | Kubiak et al. |
| 2016/0000430 A1 | 1/2016 | Ming et al. |
| 2016/0066914 A1 | 3/2016 | Baber et al. |
| 2016/0100933 A1 | 4/2016 | Linder et al. |
| 2016/0106427 A1 | 4/2016 | Shelton, IV et al. |
| 2016/0174974 A1 | 6/2016 | Schmid et al. |
| 2016/0213395 A1 | 7/2016 | Anim |
| 2016/0249919 A1 | 9/2016 | Savage et al. |
| 2016/0278765 A1 * | 9/2016 | Shelton, IV ......... A61B 17/068 |
| 2016/0345976 A1 | 12/2016 | Gonzalez et al. |
| 2017/0056000 A1 | 3/2017 | Nalagatla et al. |
| 2017/0086829 A1 | 3/2017 | Vendely et al. |
| 2017/0086837 A1 | 3/2017 | Vendely et al. |
| 2017/0231633 A1 | 8/2017 | Marczyk et al. |
| 2019/0059889 A1 | 2/2019 | Shelton, IV et al. |
| 2019/0254654 A1 | 8/2019 | Shelton, IV et al. |
| 2019/0254655 A1 | 8/2019 | Shelton, IV et al. |
| 2019/0254656 A1 | 8/2019 | Shelton, IV et al. |
| 2019/0254658 A1 | 8/2019 | Shelton, IV et al. |
| 2019/0254659 A1 | 8/2019 | Harris et al. |
| 2019/0254660 A1 | 8/2019 | Shelton, IV et al. |
| 2019/0254661 A1 | 8/2019 | Shelton, IV et al. |
| 2019/0254670 A1 | 8/2019 | Shelton, IV et al. |

FOREIGN PATENT DOCUMENTS

| | | |
|---|---|---|
| EP | 2954857 A1 | 12/2015 |
| EP | 3087931 A2 | 11/2016 |
| EP | 3132812 A1 | 2/2017 |
| EP | 3135222 A1 | 3/2017 |
| EP | 3135317 A1 | 3/2017 |
| EP | 3150134 A1 | 4/2017 |
| EP | 3150142 A2 | 4/2017 |
| EP | 3150144 A1 | 4/2017 |
| EP | 3162388 A1 | 5/2017 |
| RU | 2629239 C2 | 8/2017 |

OTHER PUBLICATIONS

European Search Report and Written Opinion for EP19158306 dated May 8, 2019 (19 pages).

European Search Report and Written Opinion for EP19158186 dated Jul. 5, 2019 (9 pages).

Shelton, IV et al., U.S. Appl. No. 15/689,198 entitled "Endocutter Control System" filed Aug. 29, 2017. (60 pages).

Ye et al. "Development of the Warp Knitted Spacer Fabrics for Cushion Applications," Journal of Industrial Textiles, 2008, vol. 37, No. 3, pp. 213-223.

International Search Report and Written Opinion for PCT/IB2019/050408 dated Jun. 5, 2019 (17 pages).

Baker et al., "The Science of Stapling and Leaks," Obesity Surgery, vol. 14, Nov. 2004, pp. 1290-1298.

Yo et al., "Buttressing of the Staple Line in Gastrointestinal Anastomoses: Overview of New Technology Designed to Reduce Perioperative Complications," Digestive Surgery, vol. 23, No. 5-6, Oct. 2006, pp. 283-291.

International Search Report and Written Opinion for PCT/IB2019/050500 dated May 17, 2019 (21 pages).

European Search Report and Written Opinion for EP Application 19158219 dated Apr. 9, 2019 (10 pages).

Partial European Search Report and Written Opinion for EP Application 19158306 dated Apr. 9, 2019 (21 pages).

European Search Report and Written Opinion for EP Application 19158301 dated Mar. 27, 2019 (7 pages).

Partial European Search Report and Written Opinion for EP Application 19158223 dated Apr. 25, 2019 (10 pages).

Wismans et al., "Characterization of Polymeric Foams," Eindhoven University of Technology. Jul. 2009 (35 pages).

* cited by examiner

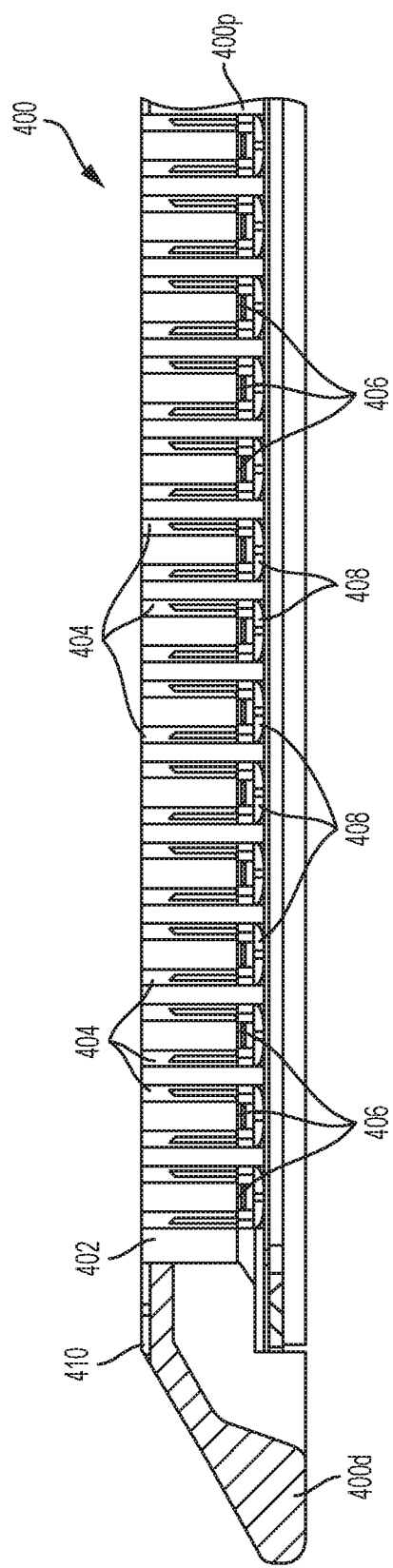
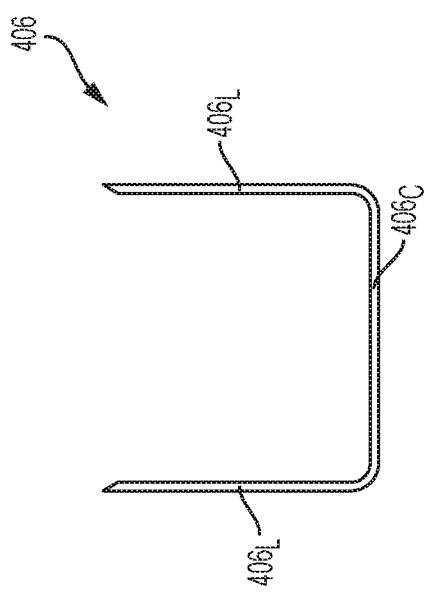
FIG. 4
FIG. 5

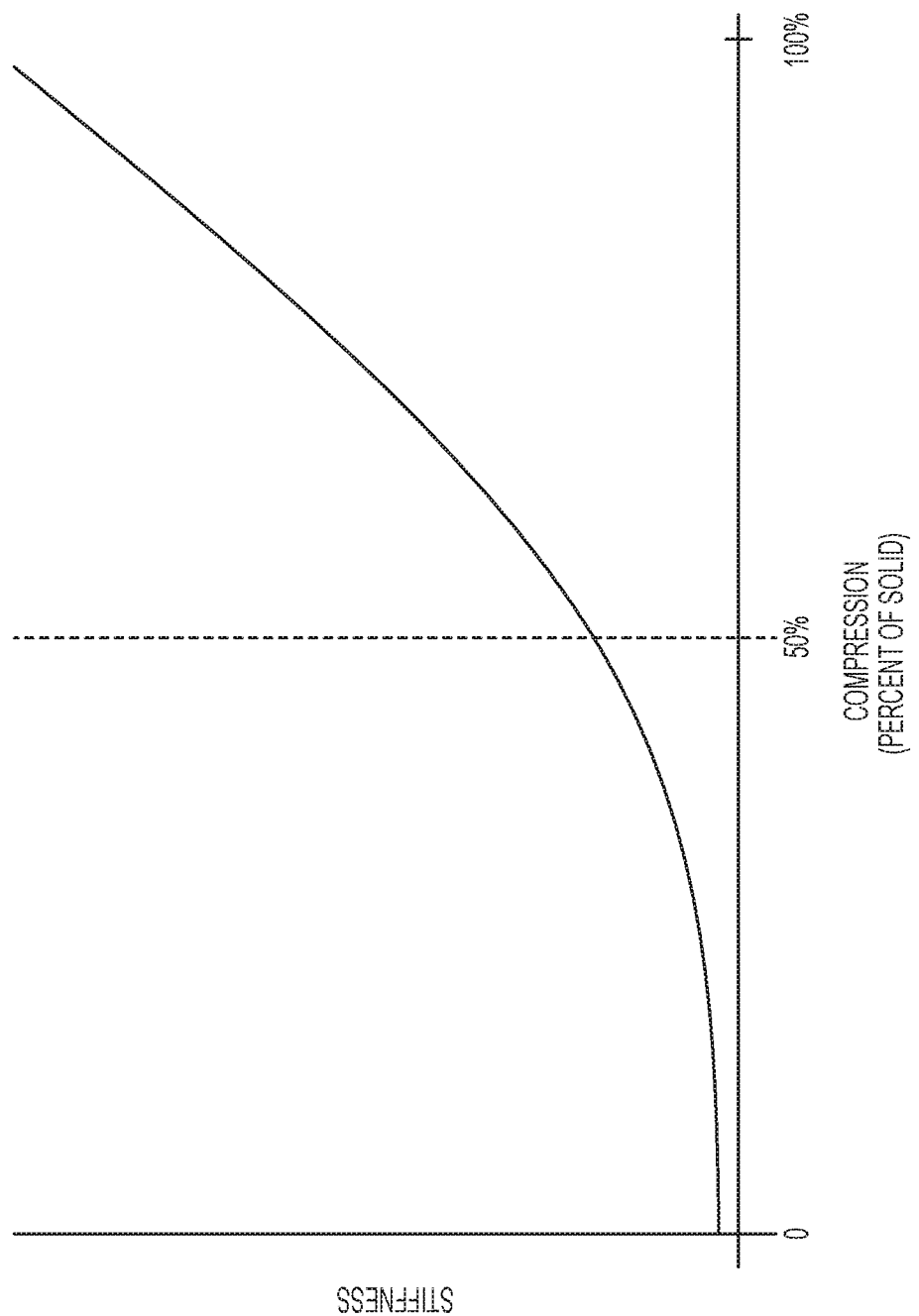

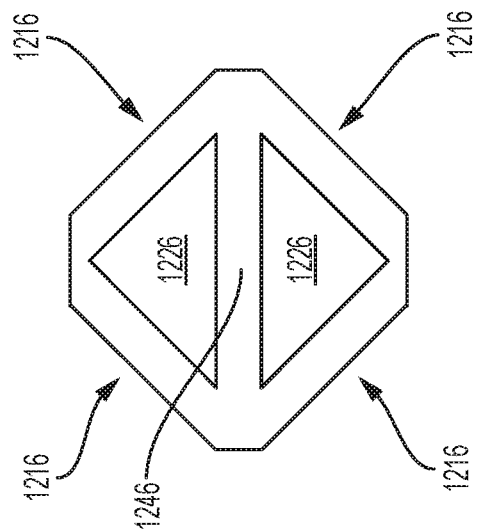
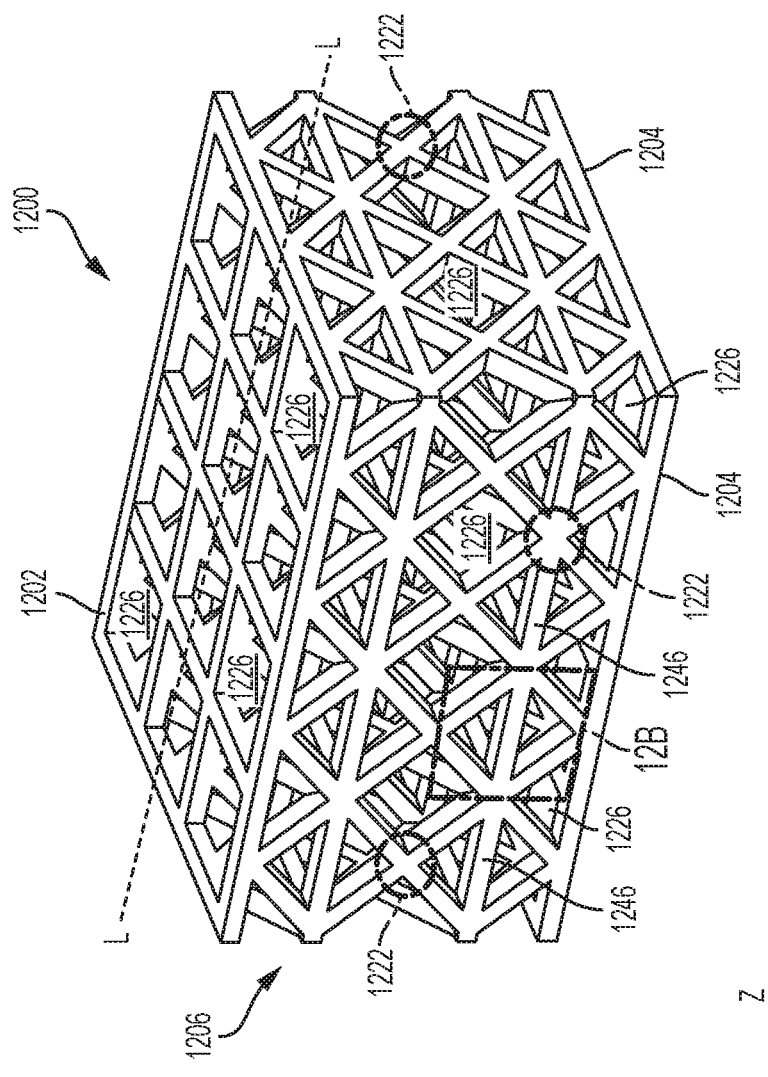
FIG. 12B
FIG. 12A

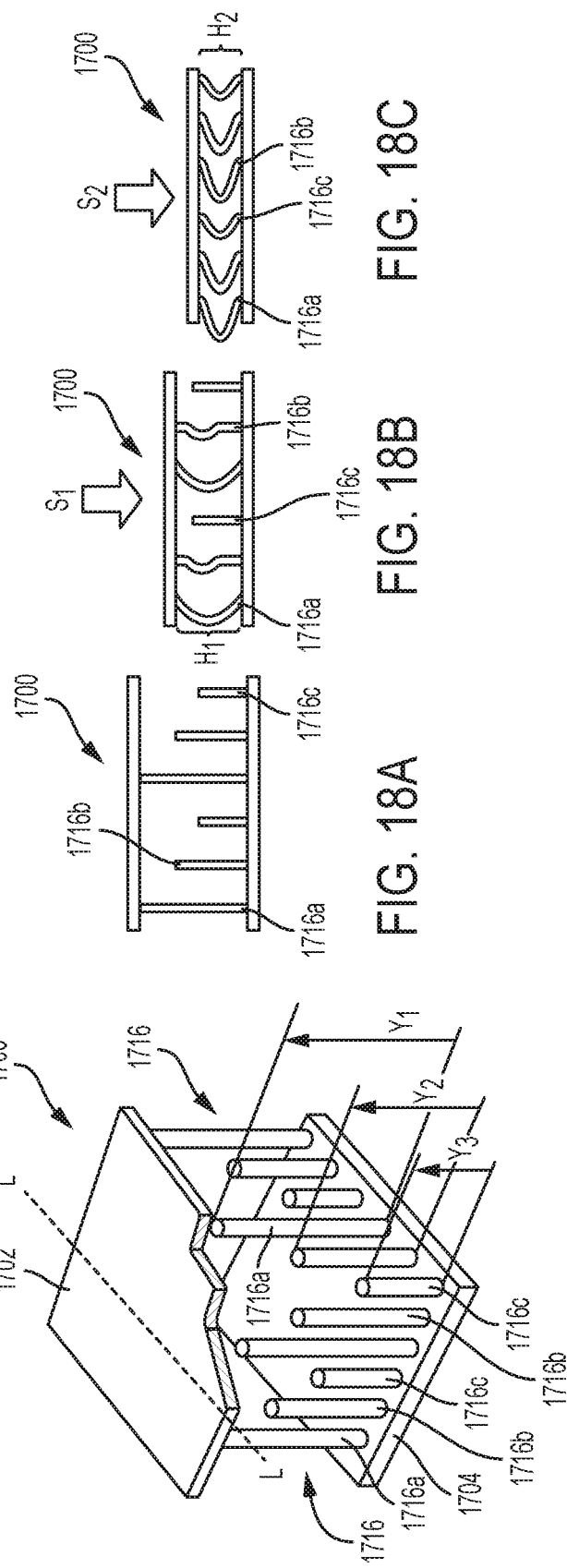

THREE DIMENSIONAL ADJUNCTS

FIELD

Three dimensional adjuncts and methods for manufacturing the same are provided.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Some surgical staplers require a surgeon to select the appropriate staples having the appropriate staple height for the tissue being stapled. For example, a surgeon could select tall staples for use with thick tissue and short staples for use with thin tissue. In some instances, however, the tissue being stapled does not have a consistent thickness and, thus the staples cannot achieve the desired fired configuration at each staple site. As a result, a desirable seal at or near all of the stapled sites cannot be formed, thereby allowing blood, air, gastrointestinal fluids, and other fluids to seep through the unsealed sites.

Further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted, and therefore are unable to withstand the varying intra-tissue pressures at the implantation site. This can lead to undesirable tissue tearing, and consequently leakage, at or near the staple site.

Accordingly, there remains a need for improved instruments and methods that address current issues with surgical staplers.

SUMMARY

Stapling assemblies for use with a surgical stapler are provided.

In one exemplary embodiment, a stapling assembly is provided and can include a plurality of staples disposed therein. The plurality of staples can be configured to be deployed into tissue. The body can have a first end, a second end, and a longitudinal axis extending therebetween. The stapling assembly can also include a three-dimensional compressible adjunct configured to be releasably retained on the body such that the adjunct can be attached to tissue by the plurality of staples in the body. The adjunct can have a first component formed from a first matrix that includes at least one fused bioabsorbable polymer, and a second component formed from a second matrix that includes at least one fused bioabsorbable polymer that differs from the at least one fused bioabsorbable polymer of the first matrix. The first and second components can be coupled to one another to form a composite structure.

In some aspects, the adjunct can be configured to apply a stress of at least about 3 g/mm$^2$ to the tissue stapled thereto for at least 3 days when the adjunct is in a tissue deployed state.

The first and second matrices can include a variety of different materials. For example, at least one of the first matrix and the second matrix can include at least two different fused bioabsorbable polymer. In one embodiment, the first matrix can include at least two bioabsorbable polymers, where a first fused bioabsorbable polymer can have a degradation rate that differs from a degradation rate of a second fused bioabsorbable polymer.

In some aspects, the at least one fused bioabsorbable polymer of the first component can be formed of polyglactin or polydioxanone. In other aspects, the at least one fused bioabsorbable polymer of the second component can be formed of a polycaprolactone copolymer.

The first and second components can have a variety of configurations. For example, the first component can be configured to bend to allow the adjunct to compress toward the body. In one embodiment, the first component can have a degradation rate that differs from a degradation rate of the second component. In another embodiment, the first component can have a first color and the second component can have a second color that differs from the first color.

In certain aspects, the first and second components can be substantially spiral-shaped. In other aspects, the first and second components can be in the form of substantially vertical columns. In one embodiment, the second component can be more flexible than the first component.

In some aspects, the first component can include a first plurality of struts that can each be substantially planar and can extend co-planar with one another in a first plane. In one embodiment, the first component can include a second plurality of struts that can each be substantially planar and can extend co-planar with one another in a second plane. The second plane can be parallel to the first plane. In another embodiment, the second component can include a plurality of rods that interconnect the plurality of struts. Each rod can extend laterally relative to the longitudinal axis of the body.

In other aspects, at least one of the first component and the second component can be at least partially coated with a bioabsorbable polymer that can be different than the at least one fused bioabsorbable polymer of the first matrix and of the second matrix. In one embodiment, the bioabsorbable polymer can have a slower degradation rate than a degradation rate of the at least one fused bioabsorbable polymer of the first matrix and of the second matrix.

In another exemplary embodiment, a stapling assembly can be provided that includes a body having a plurality of staples disposed therein. The plurality of staples can be configured to be deployed into tissue. The stapling assembly can also include a three-dimensional compressible adjunct configured to be releasably retained on the body such that the adjunct can be attached to tissue by the plurality of staples in the body. The adjunct can be a fused structure having a plurality of struts that can be interconnected at nodes. The plurality of struts can be formed of a first fused matrix, and the nodes can be formed of a second fused matrix that is more flexible than the first fused matrix.

In one aspect, the adjunct can be configured to apply a stress of at least about 3 g/mm$^2$ to the tissue stapled thereto for at least 3 days when the adjunct is in a tissue deployed state.

In some aspects, the first fused matrix can have a degradation rate that differs from a degradation rate of the second fused matrix.

In certain aspects, at least one of the first fused matrix and the second fused matrix includes at least two different fused bioabsorbable polymers. In one embodiment, the first fused matrix can include at least two fused bioabsorbable polymers in which a first fused bioabsorbable polymer can have a degradation rate that differs from a degradation rate of a second fused bioabsorbable polymer.

In one aspect, the first fused matrix can include at least one fused bioabsorbable polymer. The at least one fused bioabsorbable polymer of the first fused matrix can be polyglactin or polydioxanone. In another aspect, the second fused matrix can be formed of at least one fused bioabsorbable polymer. The at least one fused bioabsorbable polymer of the second fused matrix can be a polycaprolactone copolymer.

BRIEF DESCRIPTION OF THE DRAWINGS

This invention will be more fully understood from the following detailed description taken in conjunction with the accompanying drawings, in which:

FIG. 4 is a longitudinal cross-sectional view of a surgical cartridge that can be disposed within the stapling and severing instrument of FIG. 1;

FIG. 5 is a top view of a staple in an unfired (pre-deployed) configuration that can be disposed within the staple cartridge of the surgical cartridge assembly of FIG. 4;

FIG. 10 is a graphical illustration of the relationship between stiffness and compression of an adjunct;

FIG. 12A is a perspective view of another exemplary embodiment of an adjunct having a plurality of interconnected struts and linking members;

FIG. 12B is a magnified view of a repeating unit of the adjunct shown in FIG. 12A taken at 12B;

FIG. 17 is a perspective view of another exemplary embodiment of an adjunct that includes a plurality of struts in the form of vertical columns having different lengths;

FIG. 18A is a schematic illustration of the adjunct shown in FIG. 17 at a precompressed height;

FIG. 18B is a schematic illustration of the adjunct shown in FIG. 17 at a first compressed height;

FIG. 18C is a schematic illustration of the adjunct shown in FIG. 17 at a second compressed height;

DETAILED DESCRIPTION

Figure 1:
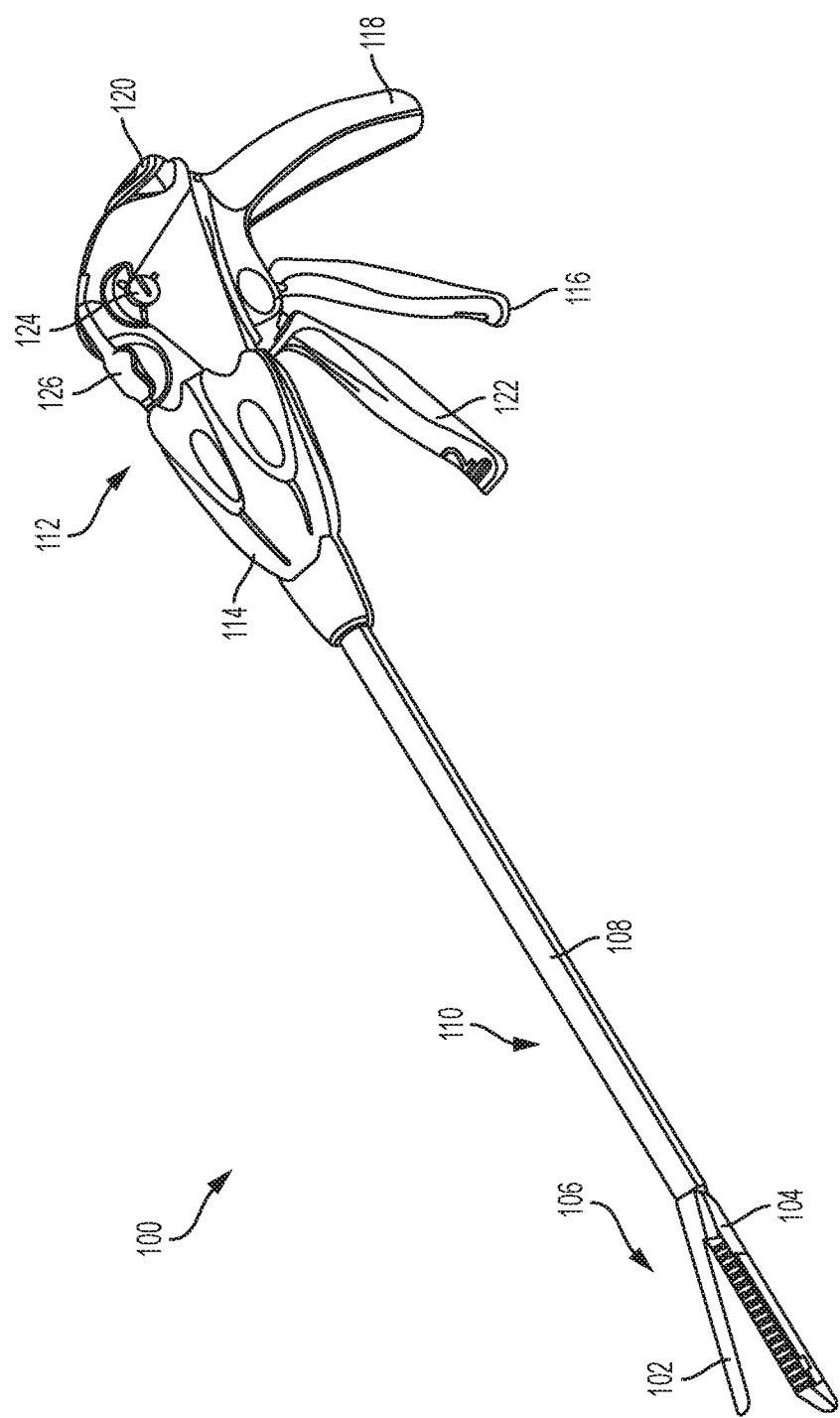
FIG. 1 is a perspective view of one exemplary embodiment of a conventional surgical stapling and severing instrument.

Certain exemplary embodiments will now be described to provide an overall understanding of the principles of the structure, function, manufacture, and use of the instruments and methods disclosed herein. One or more examples of these embodiments are illustrated in the accompanying drawings. Those skilled in the art will understand that the instruments, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, instruments, and methods, such dimensions are not intended to limit the types of shapes that can be used in conjunction with such systems, instruments, and methods. A person skilled in the art will recognize that an equivalent to such linear and circular dimensions can easily be determined for any geometric shape. Sizes and shapes of the systems and instruments, and the components thereof, can depend at least on the anatomy of the subject in which the systems and instruments will be used, the size and shape of components with which the systems and instruments will be used, and the methods and procedures in which the systems and instruments will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Values or ranges may be expressed herein as "about" and/or from/of "about" one particular value to another particular value. When such values or ranges are expressed, other embodiments disclosed include the specific value recited and/or from/of the one particular value to another particular value. Similarly, when values are expressed as approximations, by the use of antecedent "about," it will be understood that here are a number of values disclosed therein, and that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value or within 2% of the recited value.

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Surgical stapling assemblies and methods for manufacturing the same and for stapling tissue are provided. In general, a stapling assembly is provided having a body (e.g., a staple cartridge or end effector body) with a plurality of staples disposed therein. The stapling assembly also includes a three-dimensional compressible adjunct formed from a matrix that includes at least one fused bioabsorbable polymer and configured to be releasably retained on the body. The adjunct can be releasably retained to the body such that when a staple is deployed from the body and into tissue, at least a portion of the adjunct can attach to the tissue captured by the staple. As discussed herein, the adjunct can be configured to compensate for variations in tissue properties, such as variations in the tissue thickness, and/or promote tissue ingrowth when the adjunct is stapled to tissue. For example, the adjunct can be configured to apply a stress of at least about 3 g/mm$^2$ to tissue for at least 3 days when in a tissue deployed state (e.g., when the adjunct is stapled to tissue in vivo).

An exemplary stapling assembly can include a variety of features to facilitate application of a surgical staple, as described herein and illustrated in the drawings. However, a person skilled in the art will appreciate that the stapling assembly can include only some of these features and/or it can include a variety of other features known in the art. The stapling assemblies described herein are merely intended to represent certain exemplary embodiments. Moreover, while the adjuncts are described in connection with surgical staple cartridge assemblies, and need not be replaceable, the adjuncts can be used in connection with staple reloads that are not cartridge based or any type of surgical instrument.

FIG. 1 illustrates an exemplary surgical stapling and severing instrument 100 suitable for use with an implantable adjunct. The illustrated surgical stapling and severing instrument 100 includes a staple applying assembly 106 or end effector having an anvil 102 pivotably coupled to an elongate staple channel 104. The staple applying assembly 106 can be attached at its proximal end to an elongate shaft 108 forming an implement portion 110. When the staple applying assembly 106 is closed, or at least substantially closed, the implement portion 110 can present a sufficiently small cross-section suitable for inserting the staple applying assembly 106 through a trocar. While the instrument 100 is configured to staple and sever tissue, surgical instruments configured to staple but not sever tissue are also contemplated herein.

In various instances, the staple applying assembly 106 can be manipulated by a handle 112 connected to the elongate shaft 108. The handle 112 can include user controls such as a rotation knob 114 that rotates the elongate shaft 108 and the staple applying assembly 106 about a longitudinal axis of the elongate shaft 108, and a closure trigger 116 which can pivot in front of a pistol grip 118 to close the staple applying assembly 106. A closure release button 120 can be outwardly presented on the handle 112 when the closure trigger 116 is clamped such that the closure release button 120 can be depressed to unclamp the closure trigger 116 and open the staple applying assembly 106, for example.

A firing trigger 122, which can pivot in front of the closure trigger 116, can cause the staple applying assembly 106 to simultaneously sever and staple tissue clamped therein. In various instances, multiple firing strokes can be employed using the firing trigger 122 to reduce the amount of force required to be applied by the surgeon's hand per stroke. In certain embodiments, the handle 112 can include one or more rotatable indicator wheels such as, for example, rotatable indicator wheel 124 which can indicate the firing progress. A manual firing release lever 126 can allow the firing system to be retracted before full firing travel has been completed, if desired, and, in addition, the firing release lever 126 can allow a surgeon, or other clinician, to retract the firing system in the event that the firing system binds and/or fails.

Additional details on the surgical stapling and severing instrument 100 and other surgical stapling and severing instruments suitable for use with the present disclosure are described, for example, in U.S. Pat. No. 9,332,984 and in U.S. Patent Application Publication No. 2009/0090763, the disclosure of which is incorporated herein by reference in their entirety. Further, the surgical stapling and severing instrument need not include a handle, but instead a housing that is configured to couple to a surgical robot, for example, as described in U.S. application Ser. No. 15/689,198, filed on Aug. 29, 2017 to Frederick E. Shelton et al., the disclosure of which is incorporated herein by reference in its entirety.

Figure 3:
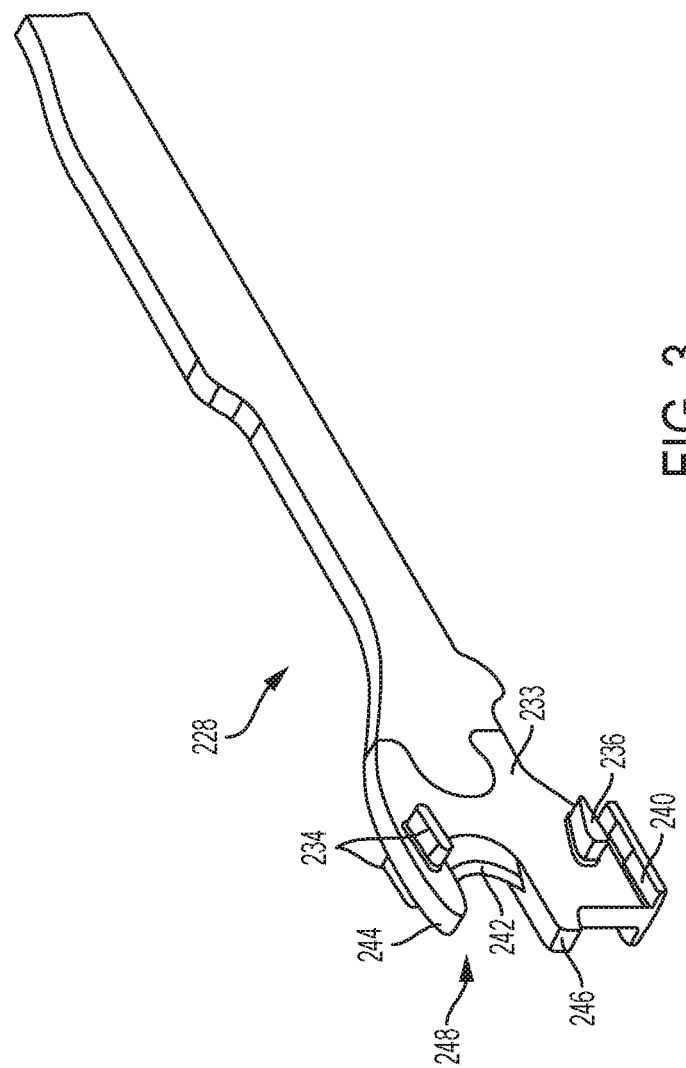
FIG. 3 is a perspective view of a knife and firing bar ("E-beam") of the surgical stapling and severing instrument of FIG. 1.
Figure 2:
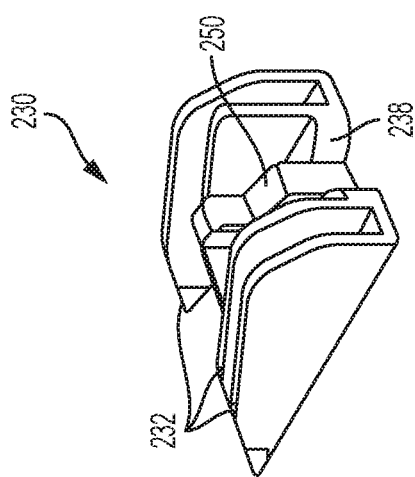
FIG. 2 is a perspective view of a wedge sled of a staple cartridge of the surgical stapling and severing instrument of FIG. 1.

With reference to FIGS. 2 and 3, a firing assembly such as, for example, firing assembly 228, can be utilized with a surgical stapling and severing instrument, such as instrument 100 in FIG. 1. The firing assembly 228 can be configured to advance a wedge sled 230 having a plurality of wedges 232 configured to deploy staples from a staple applying assembly, like staple applying assembly 106 in FIG. 1, into tissue captured between an anvil, like anvil 102 in FIG. 1, and an elongate staple channel, like channel 104 in FIG. 1. Furthermore, an E-beam 233 at a distal portion of the firing assembly 228 may fire the staples from the staple applying assembly as well as position the anvil relative to the elongate staple channel during firing. The illustrated E-beam 233 includes a pair of top pins 234, a pair of middle pins 236 which may follow portion 238 of the wedge sled 230, and a bottom pin or foot 240. The E-beam 233 can also include a sharp cutting edge 242 configured to sever the captured tissue as the firing assembly 228 is advanced distally. In addition, integrally formed and proximally projecting top guide 244 and middle guide 246 bracketing each vertical end of the cutting edge 242 may further define a tissue staging area 248 assisting in guiding tissue to the sharp cutting edge 242 prior to being severed. The middle guide 246 may also serve to engage and fire the staple applying assembly by abutting a stepped central member 250 of the wedge sled 230 that effects staple formation by the staple applying assembly.

Referring to FIG. 4, a staple cartridge 400 can be utilized with a surgical stapling and severing instrument, like surgical stapling and severing instrument 100 in FIG. 1, and can include a cartridge body 402 and a plurality of staple cavities 404 within the cartridge body 402. A staple 406 can be removably positioned in each staple cavity 404. The staple 406 in a unfired (pre-deployed, unformed) configuration is shown in more detail in FIG. 5. The staple cartridge 400 can also include a longitudinal channel that can be configured to receive a firing and/or cutting member, e.g., an E-beam, like E-beam 233 in FIG. 3.

Each staple 406 can include a crown (base) $406_C$ and one or more legs $406_L$ extending from the crown $406_C$. Prior to the staples 406 being deployed, the crowns $406_C$ of the staples 406 can be supported by staple drivers 408 positioned within the staple cartridge 400 and, concurrently, the legs $406_L$ of the staples 406 can be at least partially contained within the staple cavities 404. Further, the staple legs $406_L$ of the staples 406 can extend beyond the tissue-contacting surface 410 of the staple cartridge 400 when the staples 406 are in their unfired positions. In certain instances, as shown in FIG. 5, the tips of the staple legs $406_L$ can be sharp which can incise and penetrate tissue.

In some implementations, the staples can include one or more external coatings, e.g., a sodium sterate lubricant and/or an antimicrobial agent(s). The antimicrobial agent(s) can be applied to the staples as its own coating or incorporated into another coating, such as a lubricant. Non-limiting examples of suitable antimicrobial agents include 5-Chloro-2-(2,4-dichlorophenoxy)phenol, chlorhexidine, silver formulations (like nano-crystalline silver), lauric arginate ethyl ester (LAE), octenidine, polyhexamethylene biguanide (PHMB), taurolidine, lactic acid, citric acid, acetic acid, and their salts.

The staples 406 can be deformed from an unfired position into a fired position such that the legs $406_L$ move through the staple cavities 404, penetrate tissue positioned between an anvil, like anvil 102 in FIG. 1, and the staple cartridge 400, and contact the anvil. As the legs $406_L$ are deformed against the anvil, the legs $406_L$ of each staple 406 can capture a portion of the tissue within each staple 406 and apply a compressive force to the tissue. Further, the legs $406_L$ of each staple 406 can be deformed downwardly toward the crown $406_C$ of the staple 406 to form a staple entrapment area in which the tissue can be captured therein. In various instances, the staple entrapment area can be defined between the inner surfaces of the deformed legs and the inner surface of the crown of the staple. The size of the entrapment area for a staple can depend on several factors such as the length of the legs, the diameter of the legs, the width of the crown, and/or the extent in which the legs are deformed, for example.

In use, an anvil, like anvil 102 in FIG. 1, can be moved into a closed position by depressing a closure trigger, like closure trigger 116 in FIG. 1, to advance an E-beam, like E-beam 233 in FIG. 3. The anvil can position tissue against a tissue-contacting surface 410 of the staple cartridge 400. Once the anvil has been suitably positioned, the staples 406 can be deployed.

To deploy staples 406, as discussed above, a staple-firing sled, like sled 230 in FIG. 2, can be moved from a proximal end 400p toward a distal end 400d of the staple cartridge 400. As a firing assembly, like firing assembly 228 in FIG. 3, is advanced, the sled can contact the staple drivers 408 and lift the staple drivers 408 upwardly within the staple cavities 404. In at least one example, the sled and the staple drivers 408 can each include one or more ramps, or inclined surfaces, which can co-operate to move the staple drivers 408 upwardly from their unfired positions. As the staple drivers 408 are lifted upwardly within their respective staple cavities 404, the staples 406 are advanced upwardly such that the staples 406 emerge from their staple cavities 404 and penetrate into tissue. In various instances, the sled can move several staples upwardly at the same time as part of a firing sequence.

A person skilled in the art will appreciate that, while adjuncts are shown and described below, the adjuncts disclosed herein can be used with other surgical instruments, and need not be coupled to a staple cartridge as described. Further, a person skilled in the art will also appreciate that the staple cartridges need not be replaceable.

As discussed above, with some surgical staplers, a surgeon is often required to select the appropriate staples having the appropriate staple height for the tissue that is to be stapled. For example, a surgeon could select tall staples for use with thick tissue and short staples for use with thin tissue. In some instances, however, the tissue being stapled does not have a consistent thickness and thus, the staples cannot achieve the desired fired configuration for every section of the stapled tissue (e.g., thick and thin tissue sections). The inconsistent thickness of tissue can also lead to undesirable leakage and/or tearing of tissue at the staple site when staples with the same or substantially height are used, particularly when the staple site is exposed to intra-pressures at the staple site and/or along the staple line.

Accordingly, various embodiments of three-dimensionally printed adjuncts are provided that can be configured to compensate for varying thickness of tissue that is captured within fired (deployed) staples to avoid the need to take into account staple height when stapling tissue during surgery. That is, the adjuncts described herein can allow a set of staples with the same or similar heights to be used in stapling tissue of varying thickness (i.e., from thin to thick tissue) while also, in combination with the adjunct, providing adequate tissue compression within and between fired staples. Thus, the adjuncts described herein can maintain suitable compression against thin or thick tissue stapled thereto to thereby minimize leakage and/or tearing of tissue at the staple sites.

Alternatively or in addition, the three-dimensionally printed adjuncts can be configured to promote tissue ingrowth. In various instances, it is desirable to promote the ingrowth of tissue into an implantable adjunct, to promote the healing of the treated tissue (e.g. stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may manage the spread of infections at the surgical site, for example. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Unlike conventional adjuncts (e.g., adjuncts that are not three-dimensionally printed, such as woven adjuncts), these three-dimensionally printed adjuncts can be formed with microstructures (units) that are consistent and reproducible. That is, unlike with other methods of manufacture, 3D printing significantly improves control over microstructural features such as e.g., placement and connection of elements. As a result, variability in both the microstructure(s) and attendant properties of the adjunct is decreased, as compared to conventional woven adjuncts. For example, these three-dimensionally printed adjuncts can be structured such that they compress a predetermined amount in a substantially uniform matter. The fine control over the microstructure can also allow the porosity of the adjunct to be tailored to enhance tissue ingrowth. Further, these three-dimensionally printed adjuncts can be adapted for use with a variety of staples and tissue types.

In general, the adjuncts provided herein are designed and positioned atop a body, like cartridge body 402 in FIG. 4. When the staples are fired (deployed) from the body, the staples penetrate through the adjunct and into tissue. As the legs of the staple are deformed against the anvil that is positioned opposite the staple cartridge assembly, the deformed legs capture a portion of the adjunct and a portion of the tissue within each staple. That is, when the staples are fired into tissue, at least a portion of the adjunct becomes positioned between the tissue and the fired staple. While the adjuncts described herein can be configured to be attached to a cartridge body of a staple cartridge assembly, it is also contemplated herein that the adjuncts can be configured to mate with other instrument components, such as a jaw of a surgical stapler. A person of ordinary skill will appreciate that the adjuncts provided herein can be used with replaceable cartridges or staple reloads that are not cartridge based.

Figure 6:
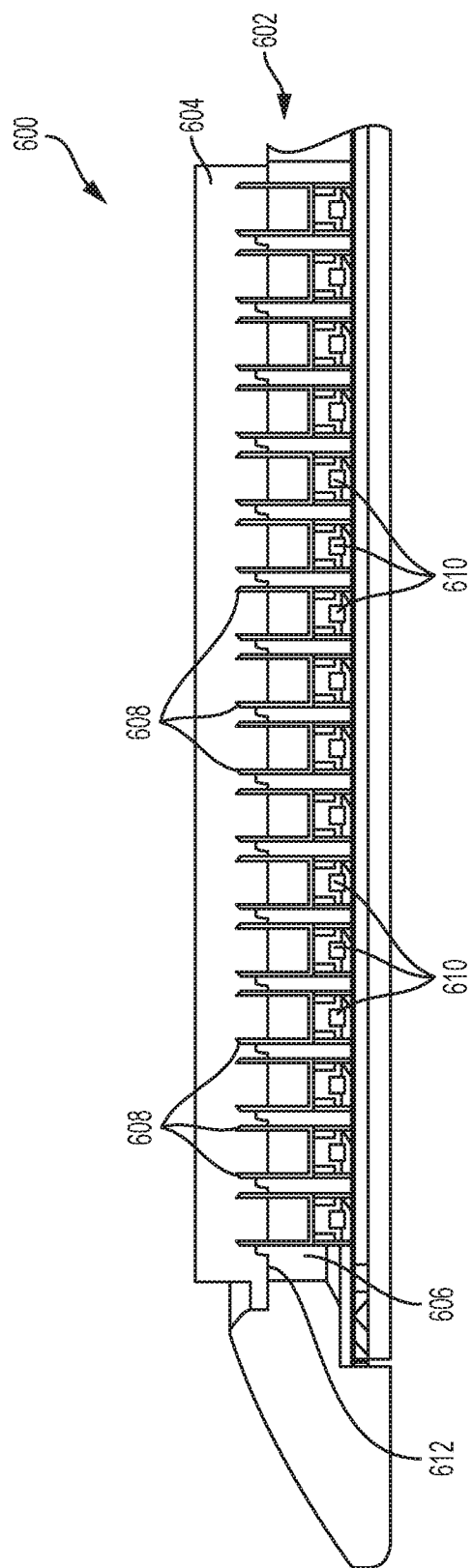
FIG. 6 is a longitudinal cross-sectional view of an exemplary embodiment of a surgical cartridge assembly having an adjunct attached to a cartridge deck.

FIG. 6 illustrates an exemplary embodiment of a staple cartridge assembly 600 that includes a staple cartridge 602 and an adjunct 604. Aside from the differences described in detail below, the staple cartridge 602 can be similar to staple cartridge 400 (FIG. 4) and is therefore not described in detail herein. As shown, the adjunct 604 is positioned against the staple cartridge 602. The staple cartridge can include a cartridge body 606 and a plurality of staples 608 disposed therein, like staples 406 shown in FIGS. 4 and 5. The staples 608 can be any suitable unformed (pre-deployed) height. For example, the staples 608 can have an unformed height between about 2 mm to 4.8 mm. Prior to deployment, the crowns of the staples 608 can be supported by staple drivers 610.

In the illustrated embodiment, the adjunct 604 can be mated to an outer surface 612, for example a tissue-contacting surface, of the cartridge body 606. In some embodiments, the outer surface 612 of the cartridge body 606 can include one or more attachment features. The one or more attachments features can be configured to engage the adjunct 604 to avoid undesirable movements of the adjunct 604 relative to the cartridge body 606 and/or premature release of the adjunct 604 from the cartridge body 606. Exemplary attachment features can be found in U.S. Patent Publication No. 2016/0106427, which is incorporated by reference herein in its entirety.

The adjunct 604 is compressible to permit the adjunct to compress to varying heights to thereby compensate for different tissue thickness that are captured within a deployed staple. The adjunct 604 has an uncompressed (undeformed), or pre-deployed, height and is configured to deform to one of a plurality of compressed (deformed), or deployed, heights. For example, the adjunct 604 can have an uncompressed height which is greater than the fired height of the staples 608 (e.g., the height (H) of the fired staple 608a in FIG. 7). That is, the adjunct 604 can have an undeformed state in which a maximum height of the adjunct 604 is greater than a maximum height of a fired staple 608a (i.e., a staple that is in a formed configuration). In one embodiment, the uncompressed height of the adjunct 604 can be about 10% taller, about 20% taller, about 30% taller, about 40% taller, about 50% taller, about 60% taller, about 70% taller, about 80% taller, about 90% taller, or about 100% taller than the fired height of the staples 608. In certain embodiments, the uncompressed height of the adjunct 604 can be over 100% taller than the fired height of the staples 608, for example.

Figure 7:
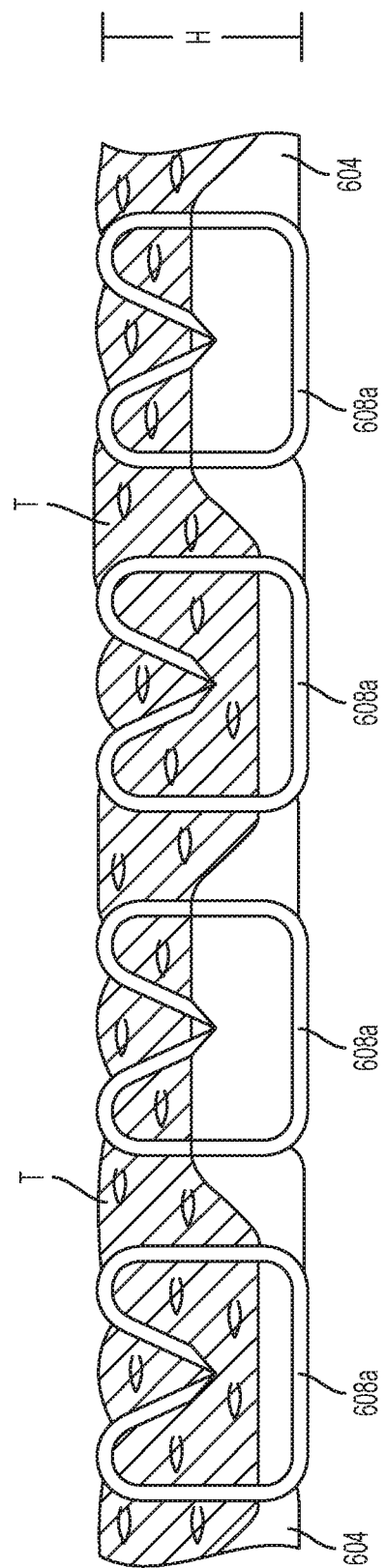
FIG. 7 is a schematic illustrating the adjunct of FIG. 6 in a tissue deployed condition.

The adjunct 604 can be releasably mated to the outer surface 612 of the cartridge body 606. As shown in FIG. 7, when the staples are fired, tissue (T) and a portion of the adjunct 604 are captured by the fired (formed) staples 608a. The fired staples 608a each define the entrapment area therein, as discussed above, for accommodating the captured adjunct 604 and tissue (T). The entrapment area defined by a fired staple 608a is limited, at least in part, by a height (H) of the fired staple 608a. For example, the height of a fired staple 608a can be about 0.160 inches or less. In some embodiments, the height of a first stapled 608a can be about 0.130 inches or less. In one embodiment, the height of a fired staple 608a can be from about 0.020 inches to 0.130 inches. In another embodiment, the height of a fired staple 608a can be from about 0.060 inches to 0.160 inches.

As described above, the adjunct 604 can be compressed within a plurality of fired staples whether the thickness of the tissue captured within the staples is the same or different within each fired staple. In at least one exemplary embodiment, the staples within a staple line, or row, can be deformed such that the fired height is about 2.75 mm, for example, where the tissue (T) and the adjunct 604 can be compressed within this height. In certain instances, the tissue (T) can have a compressed height of about 1.0 mm and the adjunct 604 can have a compressed height of about 1.75 mm. In certain instances, the tissue (T) can have a compressed height of about 1.50 mm and the adjunct 604 can have a compressed height of about 1.25 mm. In certain instances, the tissue (T) can have a compressed height of about 1.75 mm and the adjunct 604 can have a compressed height of about 1.00 mm. In certain instances, the tissue (T) can have a compressed height of about 2.00 mm and the adjunct 604 can have a compressed height of about 0.75 mm. In certain instances, the tissue (T) can have a compressed height of about 2.25 mm and the adjunct 604 can have a compressed height of about 0.50 mm. Accordingly, the sum of the compressed heights of the captured tissue (T) and adjunct 604 can be equal, or at least substantially equal, to the height (H) of the fired staple 608a.

As discussed in more detail below, the structure of the adjunct can be configured such that when the adjunct and tissue are captured within the fired staple, the adjunct can apply a stress that can withstand the pressure of circulating blood through tissue. High blood pressure is typically considered 210 mmHg, and therefore it would be desirable for the adjunct to apply a stress to the tissue that is equal to or greater than 210 mmHg (e.g., 3 g/mm$^2$) for a predetermined time period (e.g., 3 days). As such, in certain embodiments, the adjunct can be configured to apply a stress of at least about 3 g/mm$^2$ to the captured tissue for at least 3 days. The adjunct is in a tissue deployed state when the adjunct is stapled to tissue in vivo. In one embodiment, the applied stress can be about 3 g/mm$^2$. In another embodiment, the applied stress can be greater than 3 g/mm$^2$. In yet another embodiment, the stress can be at least about 3 g/mm$^2$ and applied to the captured tissue for more than 3 days. For example, in one embodiment, the stress can be at least about 3 g/mm$^2$ and applied to captured tissue for about 3 days to 5 days.

In order to design an adjunct that is configured to apply a stress of at least about 3 g/mm$^2$ to the captured tissue for a predetermined time, one can use the principles of Hooke's law (F=kD). For example, when the force (stress) to be applied to the captured tissue is known, one can design an adjunct to have a stiffness (k). The stiffness can be set by tuning the geometry of the adjunct (e.g., the diameter of the struts and/or the interconnectivity of the struts, e.g., angles and space between the struts). Further, one can design the adjunct to have a maximum amount of compression displacement for a minimum thickness of tissue, e.g., 1 mm, and therefore the length of displacement D can be the combination of a minimum thickness of tissue, e.g., 1 mm, plus a thickness of the adjunct when stapled to tissue for a given max staple height, e.g., 2.75 mm. By way of example, in one embodiment, an adjunct can be structured to have a height that is greater than a maximum formed stapled height of 2.75 mm and to compress to a height of 1.75 mm when stapled to tissue having a minimum thickness of 1 mm. Therefore, the adjunct can vary in compressibility to maintain a constant length of displacement D such that the stiffness (k) and total thickness (D) of captured tissue and adjunct can apply a stress of 3 g/mm$^2$ to the captured tissue. It should be noted a person of ordinary skill in the art will appreciate that the foregoing formula can be modified to take into account variations in temperatures, e.g., when the adjunct is brought from room temperature to body temperature after implantation.

Additionally, the adjunct can be further developed to provide a substantially continuous stress to the captured tissue (e.g., 3 g/mm$^2$) for a predetermined time (e.g., 3 days). To achieve this, one would need to take into account the degradation rate of the materials of the adjunct and the rate of tissue ingrowth within the adjunct when designing the adjunct. In doing so, one can design an adjunct such that the stiffness of the adjunct and/or the total thickness of the captured tissue and adjunct do not vary in a way that could effect an applied stress that is less than 3 g/mm$^2$.

An adjunct is stapled to tissue under various stapling conditions (e.g., tissue thickness, height of formed staple, intra-tissue pressure). Depending on the stapling condition, one can determine an effective amount of stress that the adjunct needs to be able to apply to the tissue to prevent tissue tearing and leakage. For example, in one embodiment, an effective amount of stress is at least about 3 g/mm$^2$. In order for the adjunct to provide an effective amount of stress to the tissue, the adjunct can be designed to effectively compensate for the various stapling conditions. As such, the geometry of the adjunct can be tailored to assume different compressed heights when stapled to tissue. As there is a finite range of intra-tissue pressures, tissue thicknesses, and formed staple heights, one can determine appropriate geometric structures for the adjunct that can be effective in applying a substantially continuous desired stress to the tissue (e.g., 3 g/mm$^2$) when stapled thereto for a given amount of time (e.g., at least 3 days) over a range of stapling conditions. That is, as described in more detail below, the present adjuncts are formed of compressible materials and geometrically configured so as to allow the adjunct to compress to various heights in predetermined planes when stapled to tissue. Further, this varied response by the adjunct can also allow the adjunct to maintain its application of a continuous desired stress to the tissue when exposed to fluctuations in intra-tissue pressure that can occur when the adjunct is stapled to tissue (e.g., a spike in blood pressure).

The adjuncts can be manufactured by additive manufacturing, also known as three-dimensional printing or 3D printing. 3D printing is a high-speed additive manufacturing technology that can deposit various types of materials in a printer-like fashion. That is, 3D printing is achieved by laying down successive layers of material to form shapes. To print, the printer reads the model design from a digital file and lays down successive layers of material to build a series of cross sections. These layers, as decided by the model, are joined or automatically fuse to create the final shape. This technique allows for the ability to create various shapes or geometric features with control and precision. Non-limiting examples of suitable 3D printing processes, also known as additive manufacturing, as classified by ASTM committee 42 include VAT photopolymerication (e.g., stereolithography) in which liquid photopolymer in a vat is selectively cured by light activated polymerization; material jetting in which droplets of build material are selectively deposited; binder jetting in which a liquid bonding agent is selectively deposited to join powder materials; powder bed diffusion (e.g., selective laser sintering) in which thermal energy selectively fuses regions of a powder bed; direct energy deposition in which focused thermal energy is used to fuse materials by melting as they are being deposited; direct energy deposition in which focused thermal energy is used to fuse materials by melting as they are being deposited; material extrusion (e.g., fused deposition modeling) in which material is selectively dispensed through a nozzle or orifice; and sheet lamination in which sheets of material are bonded to form an object.

For example, in some embodiments, the method can include scanning a beam to melt a plurality of layers of powder to form a compressible, bioabsorbable adjunct having an elongate body with a tissue-contacting surface, a cartridge-contacting surface that is opposite the tissue-contacting surface, and a plurality of struts forming repeating geometric units that extend between the tissue-contacting and cartridge-contacting surfaces. In one embodiment, the method can also include coating the adjunct with one or more anti-microbial agents.

The adjunct can be formed from one or more matrices. In certain embodiments, the one or more matrices can be in the form of a particulate matrix. In such instances, each particulate matrix can be formed of fused particles (e.g., fused bioabsorbable polymer particles).

In general, each matrix can be formed of at least one fused polymer. The at least one fused polymer can be selected so as to impart a desired compressibility to the adjunct. For example, in one embodiment, the matrix includes a fused polymer, whereas in other embodiments, the matrix can include two or more fused polymers that are different. Alternatively, or additionally, where the adjunct includes two or more matrices, each matrix can be formed of the same fused polymer or different fused polymers relative to each other. For example, a first matrix can include a first fused polymer and a second matrix can include a second fused polymer that is either more or less flexible than the first fused polymer. In this way, the fused polymers can provide the adjunct with varying flexibility. Further, the fused polymers can have differing degradation rates, such that the compressibility of the adjunct can be tailored to vary over time as function of the degradation rates.

While various types of materials can be used, in some embodiments, the at least one fused polymer is a bioabsorbable polymer. Non-limiting examples of suitable bioabsorbable polymers include thermoplastic absorbable polyurethane, ultraviolet curable bioabsorbable polyurethane, poly (lactic acid) (PLA), polycaprolactone (PCL), polyglycolide, polydioxanone (PDS), poly(lactic-co-glycolic acid) (PLGA), polyglycolic acid, trimethylene carbonate, glycolide, dioxanone, polyester, any copolymers thereof, or any combinations thereof. Additional non-limiting examples of suitable bioabsorbable polymers include macromers with acrylate or methacrylate end group modified three-armed hydroxyl terminated PCL or Poly (DL-lactide), PLA-PEG or poly(trimethylenecarbonate), PEG dimethyl or trimethyl acrylate or methacrylate, polypropylene fumarate, L-lactide/caprolactone copolymers, PLGA polymers infiltrated with collagen, PCL-tricalcium phosphate (TCP), PLGA-TCP copolymers coated with Hyaluronic acid, PCL-PLGA-TCP, PLGA-PCL copolymers, PDS polymers and copolymers, PCL polymer and Hyaluronic acid, PCL and Beta-Tricalcium phosphate with collagen coating, polyvinyl alcohol, calcium phosphate/poly(hydroxybutyrate-co-valerate), and calcium hydroxyapatite/poly-L-lactide.

For example, in some embodiments, the adjunct can be formed of various components each being formed of a matrix that includes at least one fused bioabsorbable polymer. In some embodiments, the adjunct can have a first component formed from a first matrix of at least one fused bioabsorbable polymer (e.g., polyglactin or polydioxanone) and a second component formed from a second matrix that includes at least one fused bioabsorbable polymer (e.g., a polycaprolactone copolymer). The at least one fused bioabsorbable polymer for each matrix can include at least two different bioabsorbable polymers. In one embodiment, the first component can have a first color and the second component can have a second color that differs from the first color.

In some embodiments, the adjunct can be drug eluting. For example, one or more components of the adjunct can include a composition having a pharmaceutically active agent. The composition may release a therapeutically effective amount of the pharmaceutically active agent. In various embodiments, the pharmaceutically active agent can be released as the adjunct is desorbed/absorbed. In various embodiments, the pharmaceutically active agent may be released into fluid, such as, for example, blood, passing over or through the adjunct. Non-limiting examples of pharmaceutically active agents include haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, and chloramphenicol; and anticancer agents, such as, for example, cisplatin, mitomycin, and adriamycin.

The adjunct can also include an external coating. The coating may be part of the 3D printing process or secondarily applied to the adjunct. For example, in some implementations, the adjunct can be partially or completely coated with antimicrobial agents. Non-limiting examples of suitable anti-microbial agents include triclosan, chlorhexidine, silver formulations (like nano-crystalline silver), lauric arginate ethyl ester (LAE), octenidine, polyhexamethylene biguanide (PHMB), taurolidine; lactic acid, citric acid, acetic acid, and their salts.

The adjunct, or any component thereof, can be at least partially coated with a bioabsorbable polymer that is different than the at least one fused bioabsorbable polymer of the adjunct. In this way, one or more properties of the adjunct can be varied from the properties of its base material(s) (e.g., fused bioabsorbable polymer(s)). For example, the adjunct can be coated with bioabsorbable polymer(s) that improve(s) structural stability. Alternatively, or in addition to, the adjunct can be coated with a bioabsorbable polymer having a slower degradation rate compared to the degradation rate of the at least one fused bioabsorbable polymer of the adjunct. In this way, the longevity of the adjunct can be increased without sacrificing the desired compressibility of the adjunct provided at least in part by the at least one fused bioabsorbable polymer.

The adjuncts can have a variety of configurations. In general, the adjuncts can include a tissue-contacting surface, an opposite body-contacting surface (e.g., a cartridge-contacting layer), and an elongate body positioned therebetween (structural layer). The tissue-contacting and cartridge-contacting surfaces can, in certain embodiments, have a structure that differs from the structural layer, so as to form tissue-contacting and cartridge-contacting layers. In some embodiments, the elongate body is formed of multiple struts. The struts can have various configurations, and in certain exemplary embodiments the struts can form interconnected repeating geometric units.

In some embodiments, the tissue-contacting layer can include a plurality of surface features thereon that are configured to engage tissue located between the adjunct and the anvil so as to substantially prevent sliding movement of the tissue relative to the adjunct during stapling. These surface features can also be configured to minimize sliding movement of the adjunct relative to the tissue when the adjunct is stapled thereto. These surface features can have a variety of configurations. For example, the surface features can extend from the tissue-contacting surface at a distance from about 0.007 inches to 0.015 inches.

Further, in some embodiments, these surface features can extend in a direction that is substantially lateral to a longitudinal axis (L) of a body, like cartridge body 606 in FIG. 6. In another embodiment, at least a portion of the surface features can include a plurality of ridges and a plurality of grooves defined between the plurality of ridges. In yet another embodiment, these surface features can include a plurality of treads extending in a direction that is at least of upwardly from a body, inwardly toward a central groove, and distally toward a second end of the body. Additional details on anti-slip features that are in the form of ridges and grooves or in the form of treads can be found in U.S. Publication No. 2015/0034696, which is incorporated by reference herein in its entirety.

In some embodiments, the plurality of surface features can be configured to pull tissue in opposite directions, and therefore provide a counter-resistance (e.g., lateral bias) to prevent the tissue from sliding during stapling. For example, the tissue-contacting layer can include a first plurality of surface features that can extend in a first direction and a second plurality of surface features that can extend in a second direction that is different than the first direction. As a result, the first and second plurality of surface features can create tension between the surface features that actively prevent motion of the tissue in at least one direction. In one embodiment, the first plurality of surface features can extend in a first direction and the second plurality of surface features can extend in an opposite second direction. In such instances, these surface features can be configured to pull tissue in opposite directions simultaneously.

A counter resistance can also be created by surface bowing. For example, the tissue-contacting layer, or in the alternative, for example, the entire adjunct, can be designed to have a resilient convex shape, and the surface features can extend radially outward from the tissue-contacting layer. In use, as the anvil of the surgical stapler moves from an open to a closed position, as discussed above, the tissue-contacting layer can deform (e.g., compress to a substantially straight configuration), and the surface features, now extending substantially vertically outward from the tissue-contacting layer, engage tissue. As the anvil returns to its open position, the tissue-contacting layer returns to its convex shape creating a surface tension between the surface features that causes the engaged tissue to be pulled in opposite directions simultaneously.

On the other hand, in certain embodiments, it can be desirable to have the tissue slide in a predefined plane during stapling. As such, in some embodiments, the tissue-contacting layer can include surface features that can be designed to promote slippage (e.g., a sliding movement) of the tissue relative to the adjunct in a first predetermined direction and to limit movement in a second direction that is different than the first direction. Alternatively, or additionally, the tissue-contacting layer can be coated with a material to increase lubricity (e.g., sodium stearate or lauric arginate ethyl ester).

As discussed above, the adjunct is positioned atop a body, like cartridge body 606 (FIG. 6). Prior to and during stapling, securement of the adjunct to the body can be enhanced. For example, the body-contacting layer (e.g., a cartridge-contacting layer) can include surface features that are configured to engage the body so as to substantially prevent sliding of the adjunct relative to the body. These surface features can have a variety of configurations. For example in embodiments where the body includes attachment features, the body-contacting layer can have surface features that are in the form of recesses that are configured to receive these attachment features. Other attachments features will be discussed in more detail below.

As indicated above, the elongated body can be formed of a plurality of struts. These struts can form repeating geometric units interconnected to one another. As discussed in more detail below, the plurality of struts and/or the array of repeating units can be structurally configured to impart a varying compressibility to the adjunct, and thus the adjunct can have a variable stiffness profile. For example, the adjunct can have a first stiffness when compressed a first amount and a second stiffness when compressed a second amount. The second amount can be greater than the first amount or vice versa. Thus, the stiffness of the adjunct can vary as a function of compression. As discussed in more detail below, the greater the amount of compression, the greater the stiffness of the adjunct. Accordingly, a single adjunct can be tailored to provide a varied response that ensures a minimum amount of stress is applied to the tissue (e.g., 3 g/mm$^2$) for at least a predetermined time (e.g., 3 days) under various stapling conditions (e.g., tissue thickness, height of formed staple, intra-tissue pressure). Further, this varied response by the adjunct can also desirably maintain the minimum amount of applied stress (e.g., 3 g/mm$^2$) when the adjunct is stapled to tissue and exposed to fluctuations in intra-tissue pressure.

Figure 15:
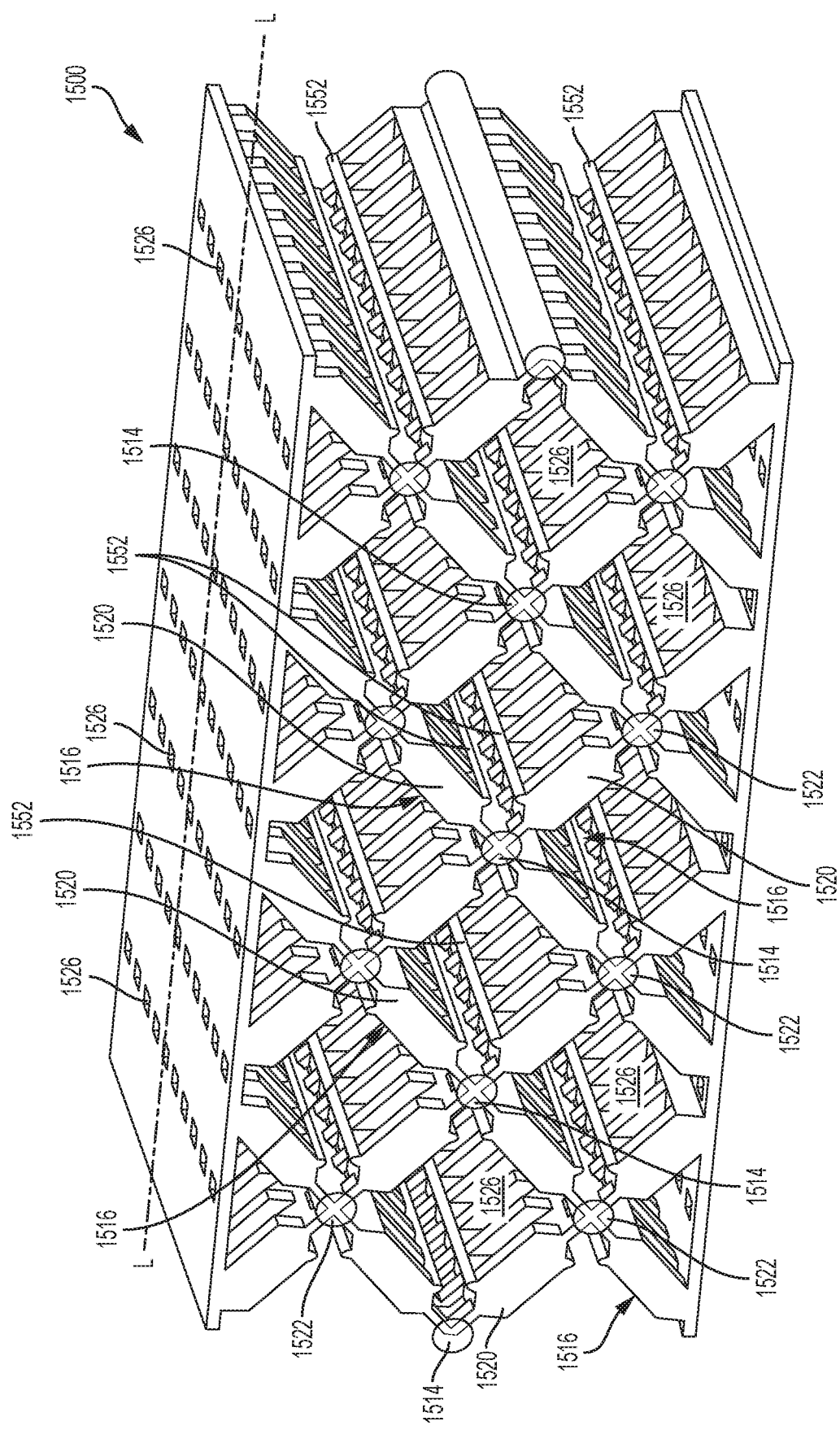
FIG. 15 is a perspective view of an adjunct according to another embodiment having a plurality of struts and at least one stopping element.
Figure 16:
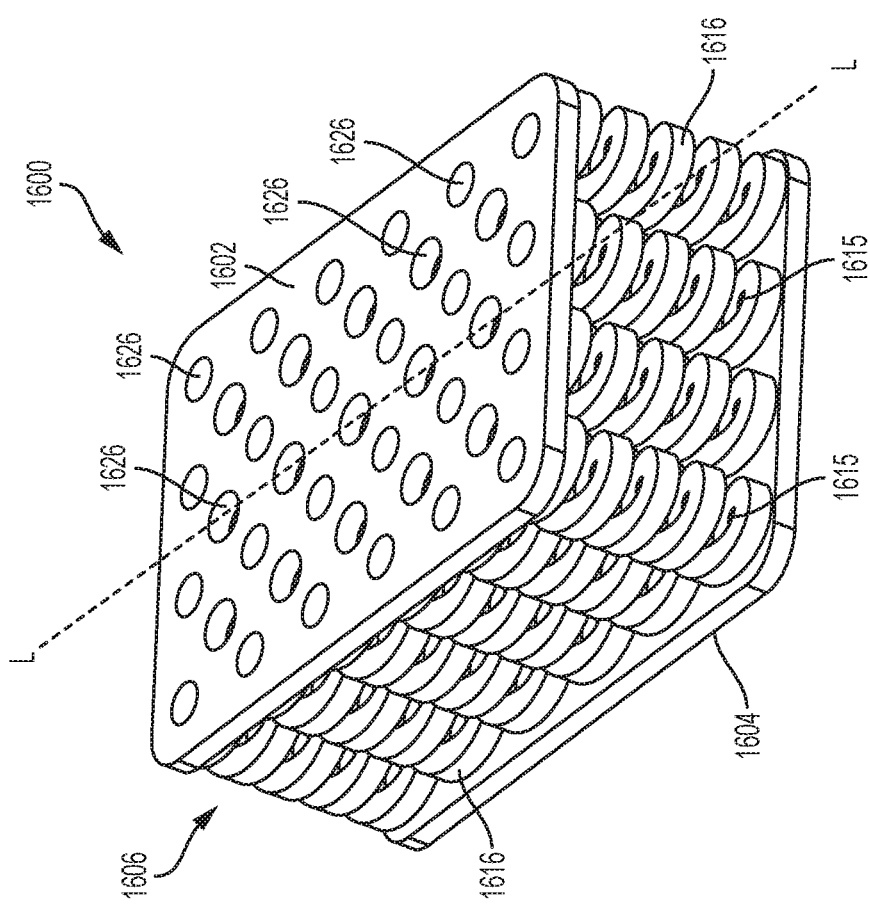
FIG. 16 is a perspective view of an exemplary embodiment of an adjunct having a plurality of struts that are substantially spiral-shaped.
Figure 19:
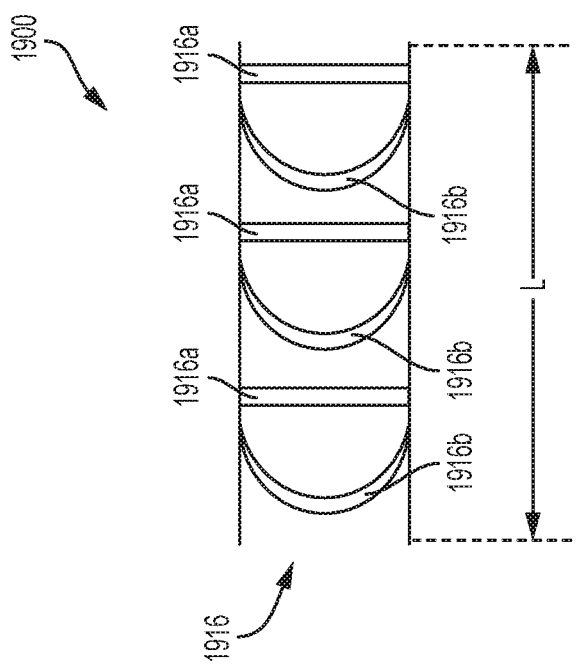
FIG. 19 is a side view of an exemplary embodiment of an adjunct that includes a plurality of struts in the form of vertical columns and curved columns.

These struts can be designed in various configurations. For example, these struts can produce lattice or truss-like structures as shown in FIGS. 8A-9C and 11A-15, spiral shaped structures as shown in FIG. 16, or columns as shown in FIGS. 17-19.

The geometry of the struts themselves, as well as the geometry of the repeating units formed therefrom, can control movement of the adjunct in various planes. For example, the interconnectivity of the struts can create geometric units that can be configured to allow the adjunct to compress in a first predetermined direction and to limit movement in a second direction that differs from the first direction. As discussed in more detail below, in some embodiments, the second direction can be transverse to the first predetermined direction. Alternatively, or in addition to, the geometric units can be configured to limit rotational movement of the adjunct about an axis that is perpendicular to the first predetermined direction.

In some embodiments, a strut can have a substantially uniform cross-section, whereas in other embodiments, the strut can have a varying cross-section. Additionally, the material of the strut can also play a role in defining movement of the adjunct in predetermined planes.

FIGS. 8A-9C and 11A-19 illustrate various exemplary adjuncts that include a tissue-contacting surface, a cartridge-contacting surface that is opposite the tissue-contacting surface, and an elongate body formed of struts positioned therebetween. Each exemplary adjunct is illustrated in partial form (e.g., not in full-length), and therefore a person of ordinary skill in the art will appreciate that the adjunct can be longer in length, i.e., along its longitudinal axis L as identified in each embodiment. The length can vary based on a length of the staple cartridge. Further, each exemplary adjunct is configured to be positioned atop a cartridge body such that the longitudinal axis L of each adjunct is aligned with and extends along the longitudinal axis ($L_C$) of the cartridge body. Each of these adjuncts can be formed from one or more matrices that include at least one fused bioabsorbable polymer. These adjuncts are structured so as to compress when exposed to compressive forces (e.g., stress or load). As discussed in further detail below, these adjuncts are also designed to promote both tissue and cellular ingrowth.

Figure 8A:
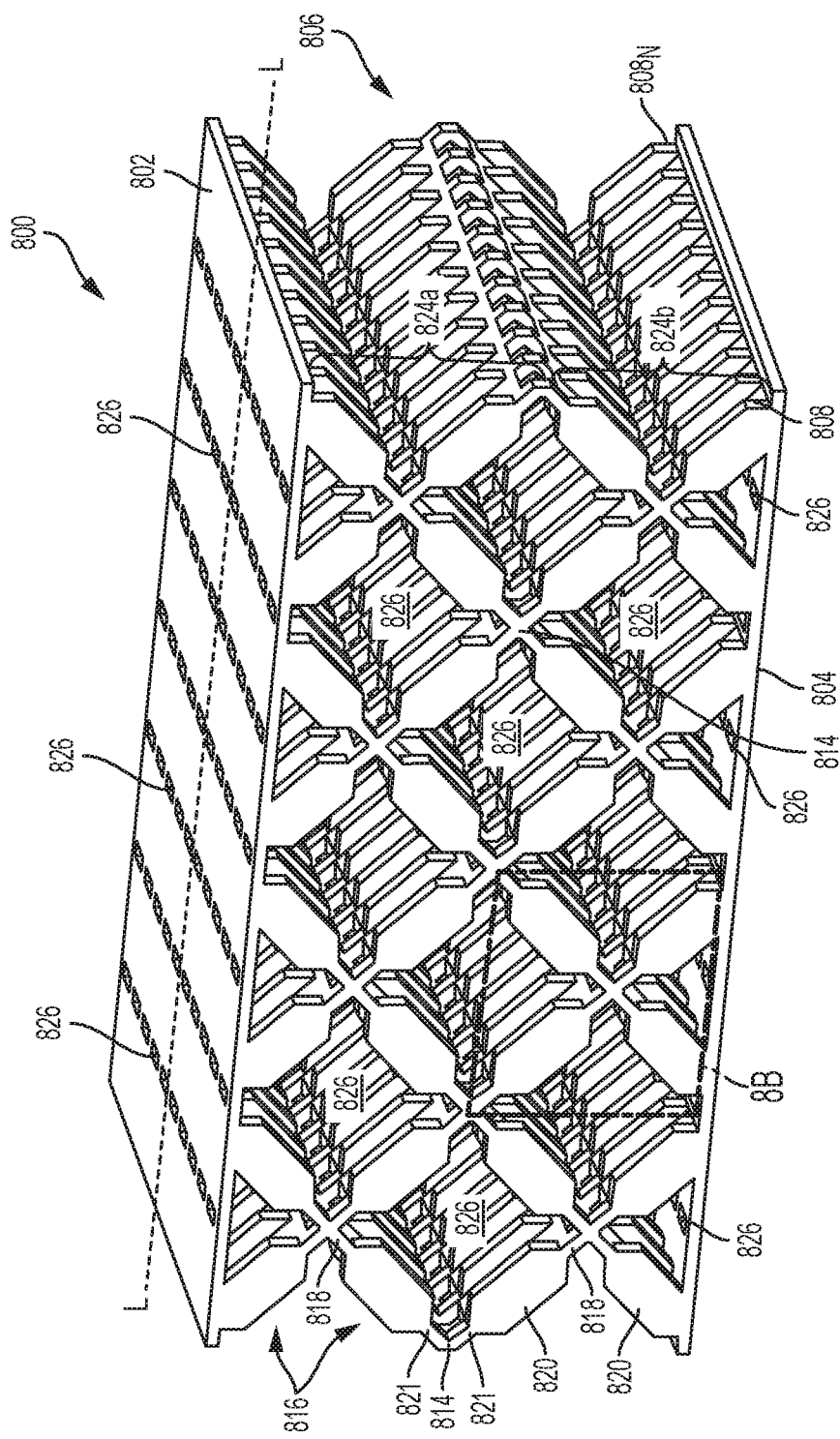
FIG. 8A is a perspective view of one exemplary embodiment of an adjunct having a plurality of repeating units of interconnected struts.
Figure 8B:
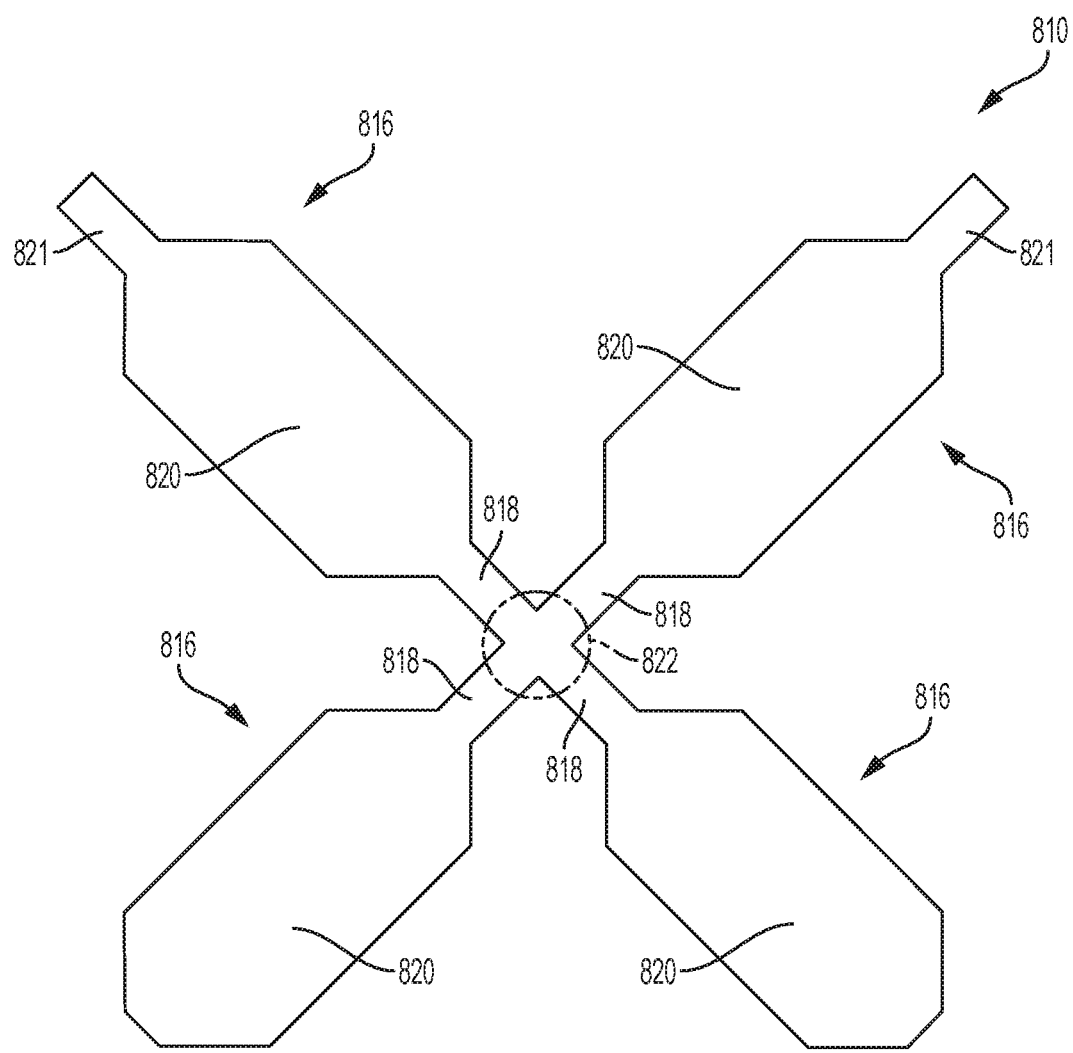
FIG. 8B is a magnified view of a repeating unit of the adjunct shown in FIG. 8A taken at 8B.

FIGS. 8A-8B illustrate an exemplary embodiment of an adjunct 800 having a tissue-contacting surface 802, an opposite cartridge-contacting surface 804, and an elongate body 806. While it is contemplated that the tissue-contacting surface 802, the cartridge-contacting surface 804, and the elongate body 806 can each be formed from different materials, in this illustrated embodiment, they are formed of the same fused bioabsorbable polymer. That is, the adjunct 800 is formed of a matrix of the same fused bioabsorbable polymer.

As shown in FIG. 8A, the elongate body 806 includes a planar array 808 of repeating units 810 interconnected to one another at joints or nodes 814. The repeating units 810 are each formed of a plurality of interconnected struts 816 that each have a first portion 818 and a second portion 820. Some of the struts 816 can also include a third portion 821 that extends from their respective second portion and interconnect to one another to form the joints or nodes 814. As discussed in more detail below, the adjunct 800 can exhibit varying stiffness and movement based on the amount and direction of stress applied thereto during use. Thus, the adjunct has a variable stiffness profile such that when the adjunct is stapled to tissue, the adjunct can be configured to apply a stress at or above a minimum stress threshold for a predetermined time (e.g., a stress of 3 g/mm² for at 3 days).

Further, as shown, the elongate body 806 includes a first planar array 808 of struts, and additional planar arrays 808$_N$ positioned parallel to one another and to planar array 808 (e.g., extending in the x-direction). In each array 808, 808$_N$, the struts 816 are substantially planar and extend co-planar with one another in a respective plane. Further, while each array 808, 808$_N$ can have a variety of configurations, in this illustrated embodiment, each array 808, 808$_N$ is substantially symmetric about a mid-plane. That is, each array 808, 808$_N$ has two substantially identical, rows 824a, 824b of repeating units 810.

While the struts 816 can have a variety of configurations, in this illustrated embodiment, each strut 816 has a generally elongate planar configuration, with the first portion 818 of each strut 816 having a narrower width than a width section of the second portion 820. As a result, the struts 816 are wider in the middle, preferably along a majority of the length, and narrower at the ends. Alternatively, the first portion 818 can have a cross section that is equal to or greater that the cross section of the second portion 820. Further, as shown in FIG. 8B, the second portion 820 of each strut 816 can have a substantially rectangular cross-sectional shape. It should be noted that other cross-sectional shapes of the struts, and portions thereof, are also contemplated herein. The cross-sectional shapes of the struts can be used to limit movement of the adjunct in certain directions.

In FIG. 8A, the struts 816 are interconnected to one another at an end of their first portion 818 to form joints or nodes 822. In the illustrated embodiment, the struts 816 and the joints or nodes 822 can be formed of the same material. Thus, to enhance the compression of the adjunct 800 under stress, the cross-section of the first portion 818, also referred to as a neck down region, can flex as described in more detail below. Further, the third portion 821 of the respective struts 816 is similarly structured like the first portion 818 of the struts 816, and therefore this third portion 821, also referred to as a neck down region, can also flex as in more detail below.

The material of the joints or nodes 822 relative to the struts 816 (e.g., more or less flexible) can control, in part, the amount and/or direction at which the adjunct 800 moves under stress during use. Likewise, the material of the joints or nodes 814 can control, in part, the amount and/or direction at which the adjunct 800 moves under stress during use. The joints or nodes 814, 822 can be any suitable shape. For example, in certain embodiments, the joints or nodes 814, 822 can be in the form of a ball-shaped feature. In other embodiments the joints or nodes 814, 822 can take the form of other geometric shapes.

The struts 816 can be interconnected to each other at various angles. For example, in this illustrated embodiment, the struts 816 intersect at about 90 degree angles relative to adjacent struts 816. In other embodiments, the struts 816 can intersect at angles in a range of about 40 degrees to 130 degrees. In another embodiment, the struts 816 can intersect at angles in a range of about 10 degrees to 90 degrees. The angles at which the struts 816 connect to each other can control, at least in part, the manner and the amount in which the adjunct 800 responds under stress. That is, the movement and stiffness of the adjunct 800 can be, at least in part, a function of these angles.

Figure 9C:
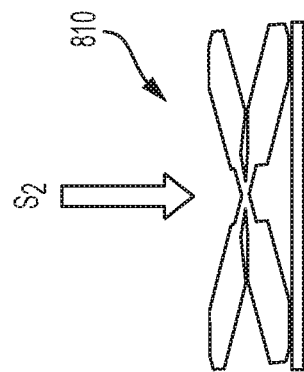
FIG. 9C is a schematic illustration of the repeating unit shown of FIG. 8B in a second compressed state.
Figure 9B:
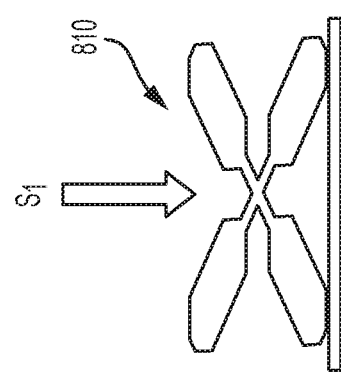
FIG. 9B is a schematic illustration of the repeating unit of FIG. 8B in a first compressed state.
Figure 9A:
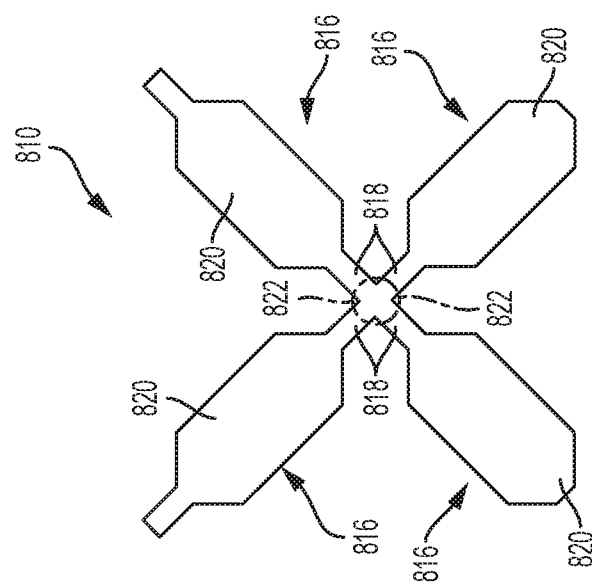
FIG. 9A is a schematic illustration of the repeating unit of FIG. 8B in a precompressed state.

As mentioned above, the first portion 818 (and the third portion 821 where present) of each strut 816 can act as a flexible region for the adjunct (e.g., a deflection point). The first portion 818 of each strut provides each repeating unit 810 with one or more bend zones, as illustrated in FIGS. 9A-9C. That is, these neck down regions allow the struts 816 to bend about or adjacent to the joints or nodes 822 when the adjunct 800 is under stress, and therefore the repeating units 810 can partially or fully collapse upon themselves. Similarly, the neck down regions that form the third portion 821 allow the repeating units to bend about or adjacent to the joints or nodes 814 when the adjunct is under stress. The compressibility of the adjunct 800 can therefore vary based on different amounts and directions of applied stress. This variation in compressibility can be desirable, for example, when the adjunct is stapled to tissue and exposed to fluctuations in intra-tissue pressure.

FIGS. 9A-9C illustrate the compression behavior of one repeating unit 810 of adjunct 800 as described herein under different stresses. In particular, the repeating unit 810 is shown in an pre-compressed (undeformed) state in FIG. 9A, a first compressed state under a first stress ($S_1$) in FIG. 9B, and a second compressed state (C) under a second stress ($S_2$) in FIG. 9C. As such, the repeating unit 810, and thus adjunct 800, has a variable stiffness profile under different stresses. A person of ordinary skill in the art will appreciate that the adjunct can have a variety of deployed heights throughout its use, and that the deployed heights are a function of, at least in part, the particular stresses that are applied to the adjunct throughout its use.

As shown in FIGS. 9A-9B, when the repeating unit 810, and thus adjunct 800 in FIG. 8A, is under a first stress $S_1$, the first portion 818 (e.g., the neck down region) of each strut 816 can bend about the joint or node 822. This allows the repeating unit 810 to compress from a pre-compressed state (FIG. 9A) to a first compressed state (FIG. 9B), and thus adjunct 800 from a pre-compressed height to a first deployed height. Further, depending on the amount of stress applied to the adjunct, the second portion 820 of adjacent struts 816 can come into contact with each other. This is illustrated in FIG. 9B. In such instances, the first portion 818 of each strut 816 has therefore reached a maximum deflection point creating a greater stiffness resistance within the repeating unit 810. This is because the stiffness of the repeating unit 810, and thus the adjunct 800, increases as the adjunct 800 compresses. FIG. 10 is an exemplary graph representation of the relationship between compression and stiffness of an adjunct. Thus, any further compression of the repeating 810, and thus the adjunct 800 would require an additional applied stress.

In circumstances where a greater stress (e.g., second stress, $S_2$) is applied to the repeating unit 810, and thus adjunct 800 in FIG. 8A, the increase in stiffness resistance can be overcome. To achieve this, the struts 816 can be configured such that when additional stress is applied, the struts 816 can further bend about the joint or node 822. As shown in FIG. 9C, this further bending can cause the struts 816 to further expand outward in a direction lateral (L) to the direction of applied stress, whereby causing the second portions 820 of adjacent struts 816 to come into further contact with each other. As a result, this allows the repeating unit 810 to compress to a second compressed state (FIG. 9C), and thus adjunct 800 to a second deployed height.

Figure 11A:
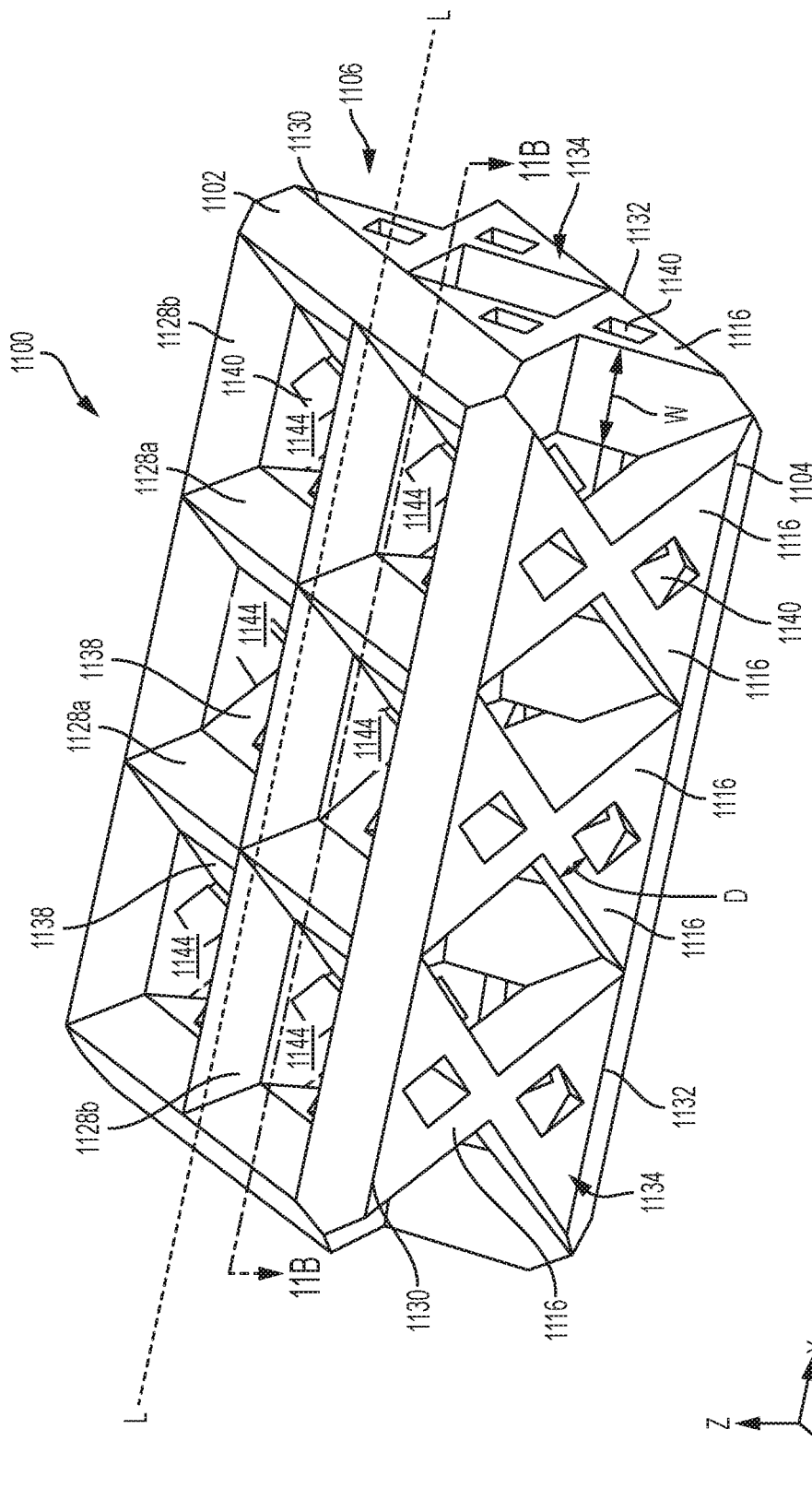
FIG. 11A is a perspective view of an exemplary embodiment of an adjunct having a plurality of interconnected struts and inner connectivity features.
Figure 11B:
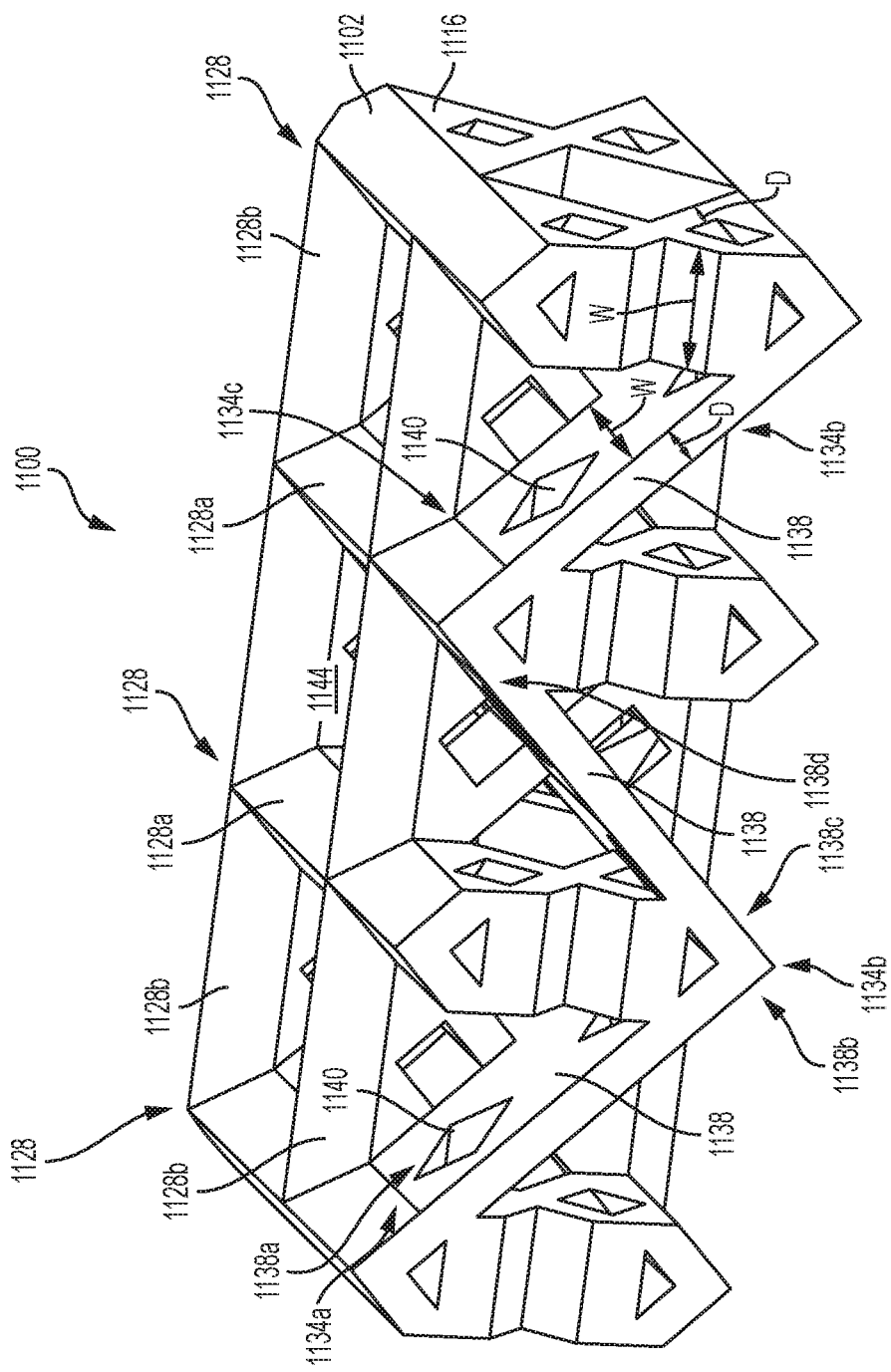
FIG. 11B is a perspective cross-sectional view of the adjunct shown in FIG. 11A taken at 11B.

In some embodiments, the adjunct can include additional components that can prevent movement of tissue that is stapled to the adjunct. For example, FIGS. 11A-11B illustrate an exemplary adjunct 1100 that includes a plurality of surface features 1128 defined within the tissue-contacting layer 1102. As described in more detail below, the surface features 1128 can prevent slidable movement of the adjunct relative to tissue stapled to the adjunct. In one embodiment, at least a portion of the surface features 1128 can prevent lateral sliding of the adjunct 1100 relative to the tissue. Alternatively, or in addition to, at least a portion of the surface features 1128 can prevent longitudinal sliding of the adjunct 1100 relative to the tissue.

The illustrated exemplary adjunct 1100 includes a tissue-contacting layer 1102 and an opposite cartridge-contacting layer 1104. The adjunct 1100 also includes an elongate body 1106 having a plurality of struts 1116 extending between the tissue-contacting layer 1102 and the cartridge-contacting layer 1104. As shown, the tissue-contacting layer 1102 includes a plurality of surface features 1128 defined therein. These surface features 1128 have a grid-like pattern with a first series 1128a extending longitudinally (e.g., parallel to the longitudinal axis of the adjunct) and a second series 1128b extending laterally (e.g., traverse to the longitudinal axis of the adjunct). Each surface feature 1128a, 1128b can have a triangular profile, or at least two surfaces that are angled relative to one another and that come together to form an edge so as to penetrate into and engage tissue. These edges collectively can define the outer-most surface of the tissue-contacting layer 1102. These surface features 1128a, 1128b can engage tissue when the tissue is compressed into the tissue-contacting layer 1102 as a result of the adjunct being stapled to tissue. The orientation of the edges of the first series 1128a can prevent lateral sliding of the adjunct relative to the tissue and the orientation of the edges of the second series 1128b can prevent longitudinal sliding of the adjunct 1100 relative to the tissue. Further, the tissue-contacting layer 1102 includes a plurality of openings 1144 that are formed between these surface features 1128. In this way, the plurality of openings 1144 can receive tissue therein when the adjunct is stapled to tissue to allow the surface features 1128 to engage the tissue.

While the plurality of struts 1116 can be interconnected to form a variety of configurations, in this illustrated embodiment, the plurality of struts 1116 form repeating X patterns. In particular, the plurality of struts 1116 form repeating cubic units. Each cubic unit includes a top surface 1130; and an opposing bottom surface 1132. In this illustrated embodiment, the top and bottom surfaces 1130, 1132 are substantially identical. The cubit unit also includes four side surfaces 1134 extending between and connecting the top and bottom surfaces 1130, 1132. In this illustrated embodiment the side surfaces 1134 are substantially identical. For clarity, not all surfaces of each illustrated cubit unit are identified in FIGS. 11A-11B. The side surfaces 1134 can have a variety of shapes, for example, as shown each side surface 1134 has an X shape that extends from the top to the bottom surfaces 1130, 1132. As such, the first end of each strut 1116 terminates at the tissue-contacting layer 1102 and the second end of each strut 1116 terminates at the cartridge-contacting layer 1104. Each X can be formed by two elongated, generally planar struts that intersect at a mid-portion. Further, each repeating cubic unit can also include an internal strut that extends between two opposite side surfaces 1134 of the cubic unit to form an inner connectivity feature 1138. As shown, the inner connectivity feature 1138 can extend from the top 1134a of one side surface 1134 to the bottom 1134b of an opposing side surface 1134. As further shown, the inner connectivity features 1138 can extend in alternating directions between adjacent cubic units. For example, as shown in FIG. 11B, a first inner connectivity feature 1138 can have an upper end 1138a that extends from the top 1134a of one side surface 1134 to a lower end 1138b at the bottom 1134b of the opposite side surface 1134, and the adjacent cubic unit can have a second inner connectivity feature 1138 with a lower end 1138c that extends from the same bottom 1134b of the side surface 1134 to an upper end 1138d at a top 1134c of an opposite side surface 1134. The inner connectivity features 1138 can provide the adjunct 1100 with a geometry that can promote predetermined directional movement of the adjunct 1100 under applied stress. For example, in one embodiment, the inner connectivity features 1138 can substantially prevent shearing of the adjunct 1100 under applied stress.

While each strut, as well as the interconnectivity features 1138, can have a variety of configurations, in this illustrated embodiment, the struts 1116 and the interconnectivity features 1138 are each in the form of a beam or column having a width (W) that is greater than a depth (D) such that each strut/interconnectivity feature is limited to bending in a predetermined direction, i.e., in and out of the plane extending along the width (W). Further, the struts 1116 and the interconnectivity features 1138 can each include at least one opening 1140 extending therethrough to facilitate bending in a predetermined direction. For clarity purposes, not all openings 1140 extending through each strut 1116 and the interconnectivity features 1138 are identified in FIGS. 11A-11B. These openings 1140 can a variety of shapes, for example, as shown, these openings 1140 are diamond shaped. It is also contemplated that the shape of the openings 1140 can vary among struts. The openings 1140 can also be aligned throughout the adjunct. For example, openings extending through opposite sidewalls spaced longitudinally along the length of the adjunct in adjacent cubic units can be aligned longitudinally, and similarly openings extending through opposite sidewalls spaced laterally along the width of the adjunct in adjacent cubic units can be aligned laterally.

Alternatively, or additionally, the adjunct can include linking members that connect at least a portion of the joints or nodes to each other to thereby increase the stiffness of the adjunct. That is, the linking members can be incorporated into the adjunct so as to prevent movement (e.g., splaying) of the adjunct in the planes in which the linking members extend.

For example, FIGS. 12A-12B illustrate an exemplary embodiment of an adjunct 1200 having linking members 1246. In particular, the adjunct 1200 includes an elongate body 1206 formed of a plurality of struts 1216 that are interconnected at joints or nodes 1222. The elongate body 1206 has a tissue-contacting surface 1202 and an opposite cartridge-contacting surface 1204. As shown, at least a portion of these joints or nodes 1222 are interconnected to each other by linking members 1246. In this illustrated embodiment, the linking members 1246 extend in a first direction (e.g., the y-direction as shown in FIG. 12) and the struts 1216 extend in a second direction that is different than the first direction (e.g., a transverse direction, such as about 45 degrees relative to the y-direction as shown in FIG. 12). Thus, the position of the linking members 1246 relative to the struts 1216 can provide the adjunct 1200 with a geometry that can be configured to prevent movement of the adjunct 1200 in at least in one direction (e.g., a direction parallel to the direction in which the linking members 1246 extend).

In some embodiments, the joints or nodes can be formed of material that differs from the material of the struts. For example, the material of the joints or nodes can be more flexible than the material of the struts, thereby increasing the compressibility of the adjunct. Further, the more flexible joints or nodes can also allow the adjunct to compress without substantially shearing. This is because the more flexible joints or nodes provide preferential bending zones for the adjunct, thereby decreasing the stiffness of the adjunct. In one embodiment, the joints or nodes can be formed of a polycaprolactone copolymer and the struts can be formed of polyglactin or polydioxanone.

Figure 13B:
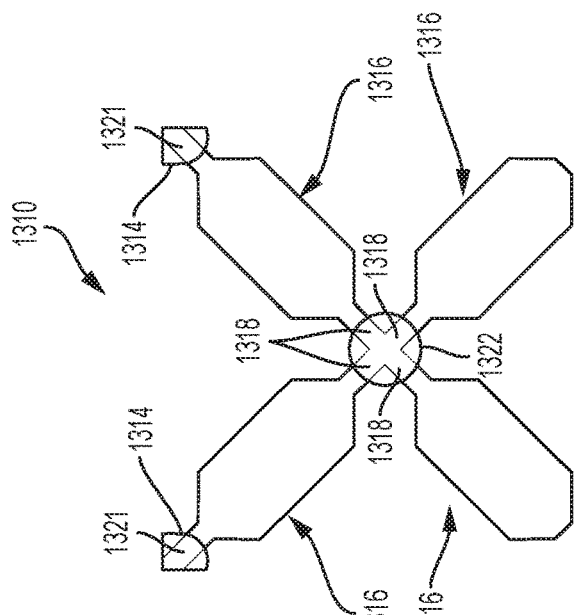
FIG. 13B is a magnified view of a repeating unit of the adjunct shown in FIG. 13A taken at 13B.
Figure 13A:
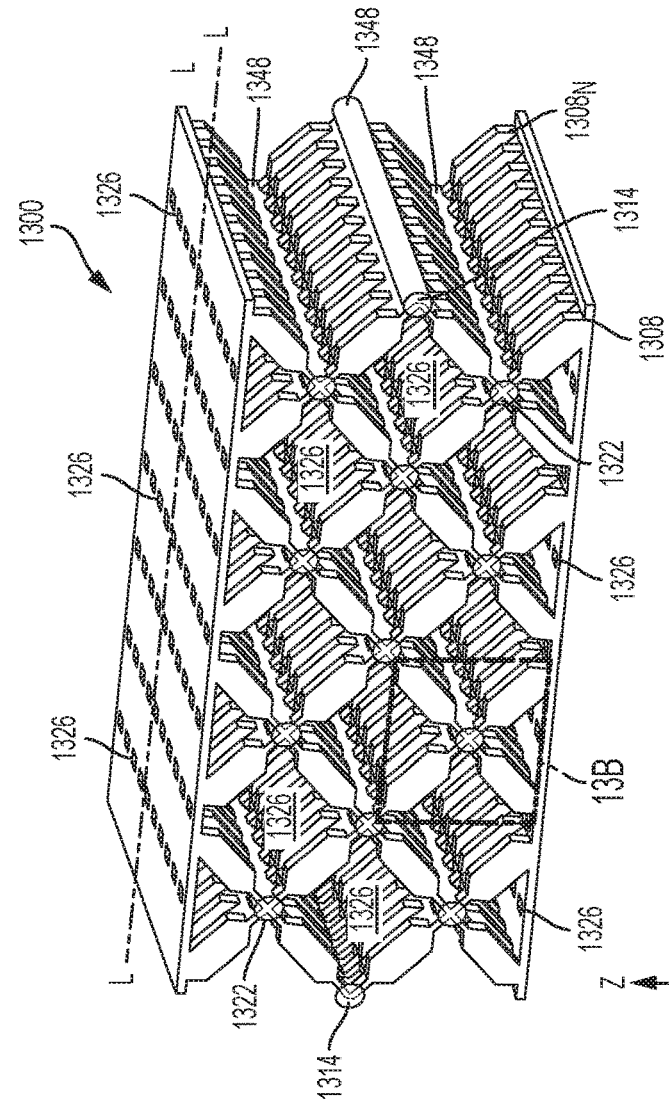
FIG. 13A is a perspective view of another exemplary embodiment of an adjunct having a plurality of struts of a first material that are interconnected at joints or nodes of a second material.

FIGS. 13A-13B illustrate another exemplary embodiment of an adjunct 1300 that includes repeating units 1310 interconnected to one another at joints or nodes 1314. The repeating units 1310 are each formed of a plurality of struts 1316, e.g., four struts, that interconnect at joints or nodes 1322. Aside from the differences described in detail below, the adjunct 1300 can be similar to adjunct 800 (FIG. 8A) and is therefore not described in detail herein. In this illustrated embodiment, the joints or nodes 1314, 1322 are formed of a different material than the material of the struts 1316. The material of the joints or nodes 1314, 1322 can be more flexible than the material of the struts 1316. As shown, each joint or node 1314, 1322 can be in the form of a rod 1348 that extends across all arrays 1308, 1308$_N$ in a direction that is generally perpendicular to the plane in which the struts extend (e.g., the rods can extend in the x-direction as shown in FIGS. 13A-13B). That is, when the adjunct 1300 is attached to a cartridge body, the rods 1348 can extend laterally relative to the longitudinal axis of a cartridge body, like cartridge body 606 in FIG. 6.

In some embodiments, as shown in FIGS. 13A-13B, the ends of the first portions 1318 of the struts 1316 can also be directly connected to each other within the joints or nodes 1322. Alternatively, or additionally, the ends of the third portions 1321 of the struts 816 can also be directly connected to each other within the joints or nodes 1314. This direct connection can help prevent the struts 1316 from pulling out of the joints or nodes 1322 as the struts 1316 bend when the adjunct 1300 is under stress. As a result of this direct connection, the bending of one strut can also influence the bending of another. Further, as compared to joints or nodes 822 in FIG. 8A, these joints or nodes 1322 can be more flexible, thus more compliant, and the adjunct 1300 can therefore compress more easily compared to adjunct 800. As such, under the same given stress, the adjunct 1300 will achieve a greater displacement (i.e., compress to a lower deployed height) as compared to adjunct 800 in FIG. 8A.

Figure 14:
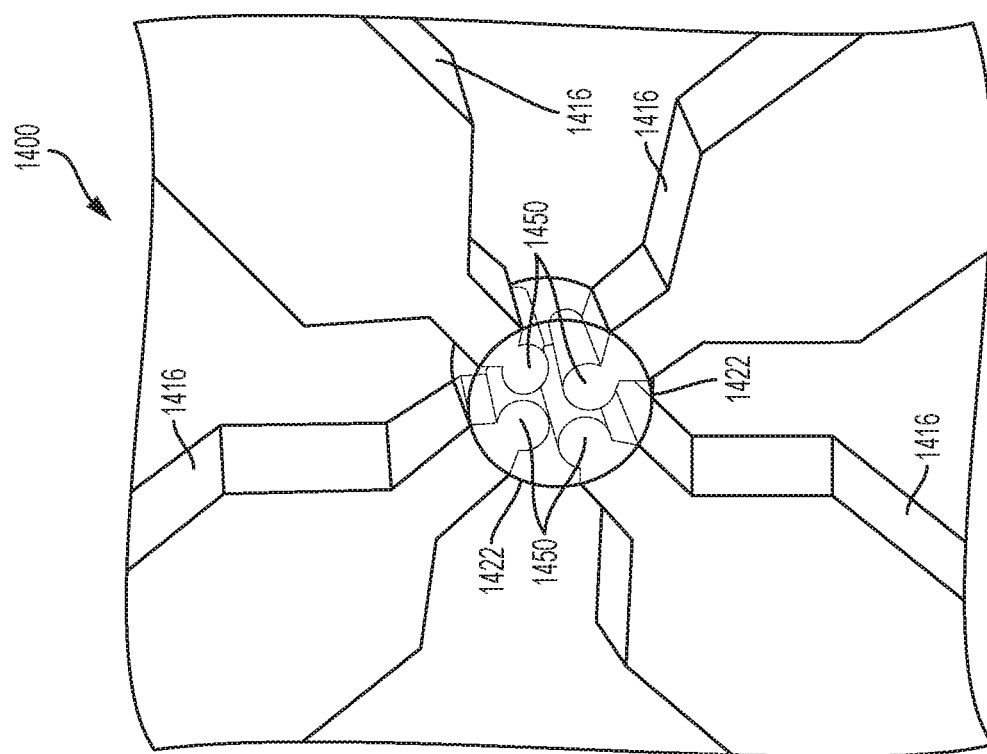
FIG. 14 is a perspective view of yet another exemplary embodiment of a repeating unit of interconnected struts with end shapes.

Alternatively, the struts can be unconnected relative to each other within the joints or nodes, for example, as shown in FIG. 14. For simplicity purposes only, FIG. 14 illustrates a single repeating unit 1400. In this illustrated embodiment, the struts 1416 do not directly connect to one another within the joint or node 1422. As a result, the bending of one strut can occur independent of the bending of another strut. To prevent the struts 1416 from pulling out of the joint or node 1422 when the struts 1416 bend thereabout, each strut 1416 can have an end shape 1450 configured to maintain its connection to the joint or node 1422. Further, as compared to joints or nodes 1322 in FIGS. 13A-13B, this joint or node 1422 can be more flexible, and thus more compliant, and therefore an adjunct formed of various repeating units 1400 can compress more easily under a given stress. That is, under the same given stress, an adjunct with this illustrated strut and joint or node configuration can achieve a greater displacement (i.e., compress to a lower height) as compared to adjunct 800 in FIGS. 13-13A.

In some embodiments, the adjunct can also include at least one stop element that is configured to limit the amount of compression of the adjunct. FIG. 15 illustrates an exemplary embodiment of an adjunct 1500 having at least one stop element 1552. Aside from the differences described in detail below, the adjunct 1500 can be similar to adjunct 1300 (FIGS. 13A-13B) and is therefore not described in detail herein.

In FIG. 15, each strut 1516 can have a stop element 1552 extending from or positioned adjacent to a surface of its second portion 1520. As the adjunct 1500 is compressed, the struts 1516 can bend about the joint or nodes 1514, 1522 until the stop elements 1552 come into contact with each other. Once these stop elements 1552 abut one another, any further bending of the struts 1516 will be inhibited. That is, these stop elements 1552 act as deflection stops that allow the adjunct 1500 to compress under a given stress to a first deployed height at a first stiffness. Upon reaching the first compressed height, the stop elements 1552 bottom out and inhibit further deflection of the struts 1516, and thus further compression of the adjunct 1500. Once the stop elements 1552 bottom out, a greater amount of stress needs to be applied to effect further bending of the struts 1516 about the joints or nodes 1514, 1522 and thus further compression of the adjunct 1500.

It should be noted that while various stop elements 1552 are shown in FIG. 15, it is contemplated herein that fewer or additional stop elements can be included throughout the adjunct 1500. Further, the shape, size, and location of the stop elements 1552 are not limited by this illustrated embodiment, and therefore can vary to control the desired amount of compression.

As mentioned above, the elongated body can include a plurality of struts that can have a variety of shapes. For example, FIG. 16 illustrates an exemplary adjunct 1600 having an elongate body 1606 that includes a plurality of struts 1616 that are substantially spiral-shaped. As such, each repeating geometric unit is in the form of a spiral or coil. In this embodiment, the elongate body 1606 is positioned between a tissue-contacting layer 1602 and a cartridge-contacting layer 1604. As shown, each layer 1602, 1604 are generally planar solid layers with openings 1626. At least a portion of these openings 1626 are aligned with the openings 1615 defined by each strut 1116. The thickness of each layer can vary. The struts 1616 are configured to have predetermined compressed heights to limit an amount of compression of the adjunct. Further, given their shape, these struts 1616 can be configured to function as a spring. Thus, similar to a spring constant, a specific stiffness can be imparted to each strut 1616 based on its shape. Thus, the compressibility of the adjunct 1600 can also be dependent on the specific stiffness of each strut 1616, which is dependent on both the material and shape of the strut 1616.

As shown in FIGS. 8A, 11A-13B, and 15-16, each adjunct 800, 1100, 1200, 1300, 1500, 1600 can include openings 826, 1140, 1144, 1226, 1326, 1526, 1626. These openings can be configured to promote cell ingrowth within each adjunct. The openings can define a void content of the adjunct. In some embodiments, the void content can be from about 15% to 95%, whereas in other embodiments, the void content can be from about 75% to 90%. As used herein, "openings" is used synonymously with "voids". Further, the adjunct can have a surface area to volume ratio of about 1:100 to 1:5. In some embodiment, the adjunct can have a surface area to volume ratio of about 1:10.

The openings can also be located within various components of the adjuncts. Each opening can have a dimension extending at least partially through the component. In certain embodiments, as shown in FIGS. 8A, 11A-13B, and 15-16, the openings 826, 1144, 1226, 1326, 1526, 1615, 1626 can be present within the tissue-contacting surface or layer, the cartridge contacting surface or layer, and/or the elongated body. In these illustrated embodiments, these openings extend completely through its respective component. Within the elongate body, these openings can be defined by the interconnected struts. Further, these openings can also be interconnected throughout the adjunct to thereby form a substantially continuous network of openings or channels. Further, as shown in FIGS. 11A-11B, openings 1140 can also be present within inner connectivity features 1138.

The openings can have varying sizes and/or shapes. For example, larger openings can allow tissue (and cells) to penetrate into the adjunct while smaller openings can trap cells within the adjunct to promote cell ingrowth. In this way, the variable opening sizes throughout the adjuncts can promote extracellular remodeling. That is, the variable opening sizes can facilitate revascularization as well as mobility of cells within the adjunct when the adjunct is implanted, thereby encouraging both tissue and cellular ingrowth. Further, the variable opening sizes can also facilitate extraction of byproducts and cellular waste from the implanted adjunct, and thus the implantation site. In some embodiments, the openings are substantially circular-shaped.

In embodiments where openings are located within the tissue-contacting surface or layer and the elongate body, such as in FIGS. 8A, 11A-13B, and 15-16, the openings can each have a diameter that is about 70% to 170% of a diameter of a staple leg of a staple, like staple 406 in FIGS. 4-5. The openings within the tissue-contacting surface and within the elongate body can have a variety of sizes. For example, in some embodiments, the openings in the tissue-contacting surface can each have a diameter in the range of about 100 μm to 1000 μm. In one embodiment, the openings in the tissue-contacting surface can each have a diameter that is at least about 14 μm. The openings in the elongate body can each have a diameter in the range of about 200 μm to 610 μm or of about 400 μm to 1000 μm. As used herein, "diameter" of an opening is the largest distance between any pair of vertices of the opening.

Further, in some embodiments, the openings within the tissue-contacting surface or layer can be configured to allow one or more portions of tissue to penetrate or compress into the tissue-contacting surface or layer (e.g., openings 1144, 1226, 1626). In this way, as discussed above, when the adjunct is stapled to tissue and the tissue is compressed into the opening, slidable movement of adjunct relative to the tissue can be substantially prevented.

In other embodiments, the adjunct can be configured to enhance staple leg advancement through the adjunct. For example, the adjunct can have openings that are aligned with the advancement direction of the staple legs into and partially through the adjunct. The openings can extend partially or completely through the adjunct. Thus, as the staple legs advance through the adjunct, the openings can act as a guide to minimize damage to the staple, as well as the adjunct, as the staple passes therethrough.

In some embodiments, as shown in FIGS. 17-19, the adjunct can include a plurality of struts that are in the form of columns. For example, in FIG. 17, the columns can be substantially vertical and of varying heights. Further, in other embodiments, as shown in FIG. 19, a first set of columns can be substantially vertical and a second set of columns can be curved. The struts can be formed of the same or different material. In some embodiments, the adjunct can include a first plurality of struts that are formed of a first material and a second plurality of struts that are formed of a second material.

In FIG. 17, the adjunct 1700 includes a plurality of struts 1716 that are in the form of substantially vertical columns. In particular, these struts 1716 extend from a cartridge-contacting layer 1704 toward, and in some instances to, the opposing tissue-contacting layer 1702. The plurality of struts 1716 includes a first plurality of vertical struts 1716a having a first height ($Y_1$), a second plurality of struts 1716b having a second height ($Y_2$) that is less than the first height ($Y_1$), and a third plurality of struts 1716c having a third height ($Y_3$) that is less than the second height ($Y_2$). For simplicity, only a portion of the plurality of struts 1716 are shown in FIG. 17. While not shown, a person of ordinary skill will appreciate that the tissue- and/or cartridge contacting layers 1702, 1704 can include openings as discussed herein.

The varying heights of these plurality of struts 1716 can provide the adjunct with varying compressibility. FIGS. 18A-18C illustrate the compression behavior of adjunct 1700 under different stresses. In particular, the adjunct 1700 is shown at a pre-compressed height in FIG. 18A, a first compressed height ($H_1$) under a first stress ($S_1$) in FIG. 18B, and a second compressed height ($H_2$) under a second stress ($S_2$) in FIG. 18C. As shown, the first compressed height ($H_1$) is greater than the second compressed height ($H_2$), and therefore the first stress ($S_1$) is less than the second stress ($S_2$). A person of ordinary skill in the art will appreciate that the adjunct can have a variety of compressed heights throughout its use, and that the compressed heights are a function of, at least in part, the particular stresses that are applied to the adjunct throughout its use.

As shown in FIGS. 18A-18C, as the compression of the adjunct 1700 increases, the amount of stress needed to achieve such compresses increases. This is because additional struts are engaged as the adjunct 1700 compresses, thereby increasing the stiffness resistance of the adjunct 1700. For example, as shown in FIG. 18B, at a first stress $S_1$ applied to the adjunct 1700, the first and second plurality of struts 1716a, 1716b are engaged. In comparison, when the adjunct 1700 is under a second stress $S_2$, the first, second, and third plurality of struts 1716a, 1716b, 1716c are engaged, thereby creating a greater stiffness resistance.

Figure 20:
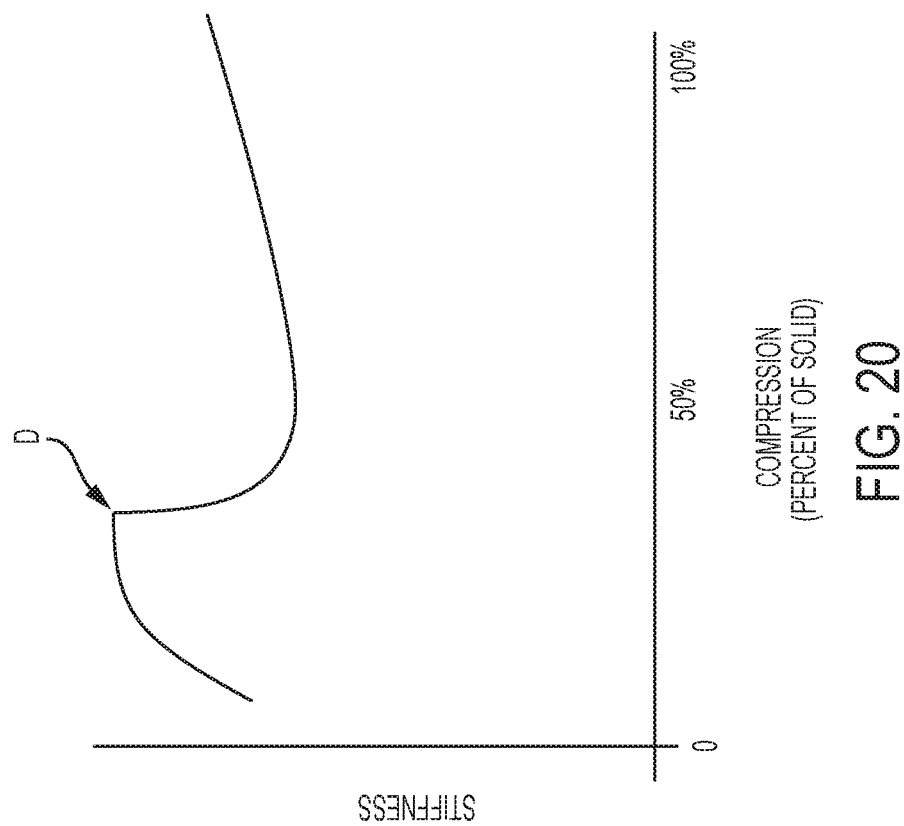
FIG. 20 is a graphical representation of the mechanical behavior of the adjunct shown in FIG. 19 over a compression range.

FIG. 19 illustrates another exemplary embodiment of an adjunct 1900 having a plurality of struts 1916 that are in the form of substantially vertical columns 1916a or curved columns 1916b. The substantially vertical columns 1916a can be configured to support the initial stress applied to the adjunct 1900, and then deflect or buckle (e.g., at deflection point D in FIG. 20) as the adjunct compresses. The curved columns 1916b can configured to provide approximately constant stiffness (i.e., essentially the offset of the whole curve shown in FIG. 20 from the zero axis). This mechanical behavior of the struts 1916, and thus the adjunct 1900, is graphically represented in FIG. 20.

Figure 21A:
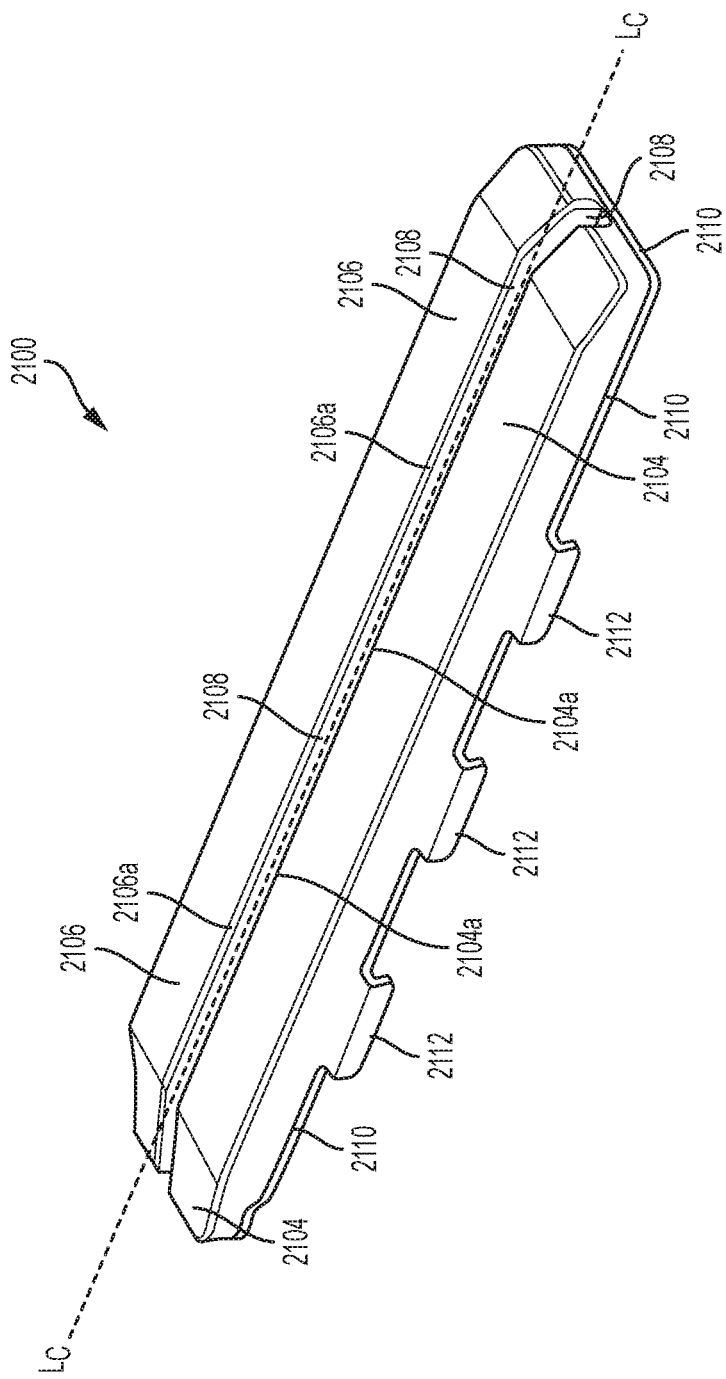
FIG. 21A is a perspective view of another exemplary embodiment of an adjunct having a channel configured to receive a cutting element and having tabs for attaching the adjunct to a staple cartridge.

In other embodiments, the adjunct can include additional features. The following figures illustrate features that can be included on any of the adjuncts disclosed herein, and thus the specific configuration of the adjunct, i.e., the configuration of the repeating units, is not shown. FIG. 21A illustrates one embodiment of an adjunct 2100 having a channel 2108 formed therein that is configured to receive a cutting element, such as a knife.

As shown in FIG. 21A, the adjunct 2100 includes a first portion 2104 and a second portion 2106, each having outer and inner edges. The inner edges 2104a, 2106a define a channel 2108 that extends between the first and second portions and along the longitudinal axis (L) of the adjunct 2100. The channel 2108 is configured to receive a cutting member, such as a knife. As shown in FIG. 121B, the channel 21 does not extend completely through the height of the adjunct 2100. In particular, the channel 2108 does not extend through the cartridge-contacting surface 2110. In this way, the adjunct 2100 is configured to have sufficient structural integrity to thereby be effectively manipulated and attached to a cartridge body, like cartridge body 2214 in FIG. 21B. In use, when the cutting member is initially fired and travels along the adjunct, the cutting member cuts through the channel, thereby separating the first and second portions, and thus separating the adjunct 2100 into two separate pieces.

Further, as shown in FIG. 21A, the adjunct 2100 includes flanges 2112 that are configured to mate with a cartridge body 2214 in FIG. 21B, as further described below. While FIG. 21A illustrates the adjunct 2100 having flanges 2112 at one side of the adjunct 2100, additional flanges 2112 can be present on the opposite side of the adjunct 2100. A person skilled in the art will appreciate that the number and placement of flanges 2112 are not limited to what is shown in FIG. 21A. While the flanges 2112 can be made of a variety of materials, in some implementations, as shown in FIG. 21A, the flanges 2112 can be an extension of the cartridge-contacting surface 2110. A person skilled in the art will appreciate that the flanges can be formed in-line with the adjunct (e.g., as part of the 3D printing process), or in the alternative formed off-line and then secondarily applied to the adjunct.

Figure 21B:
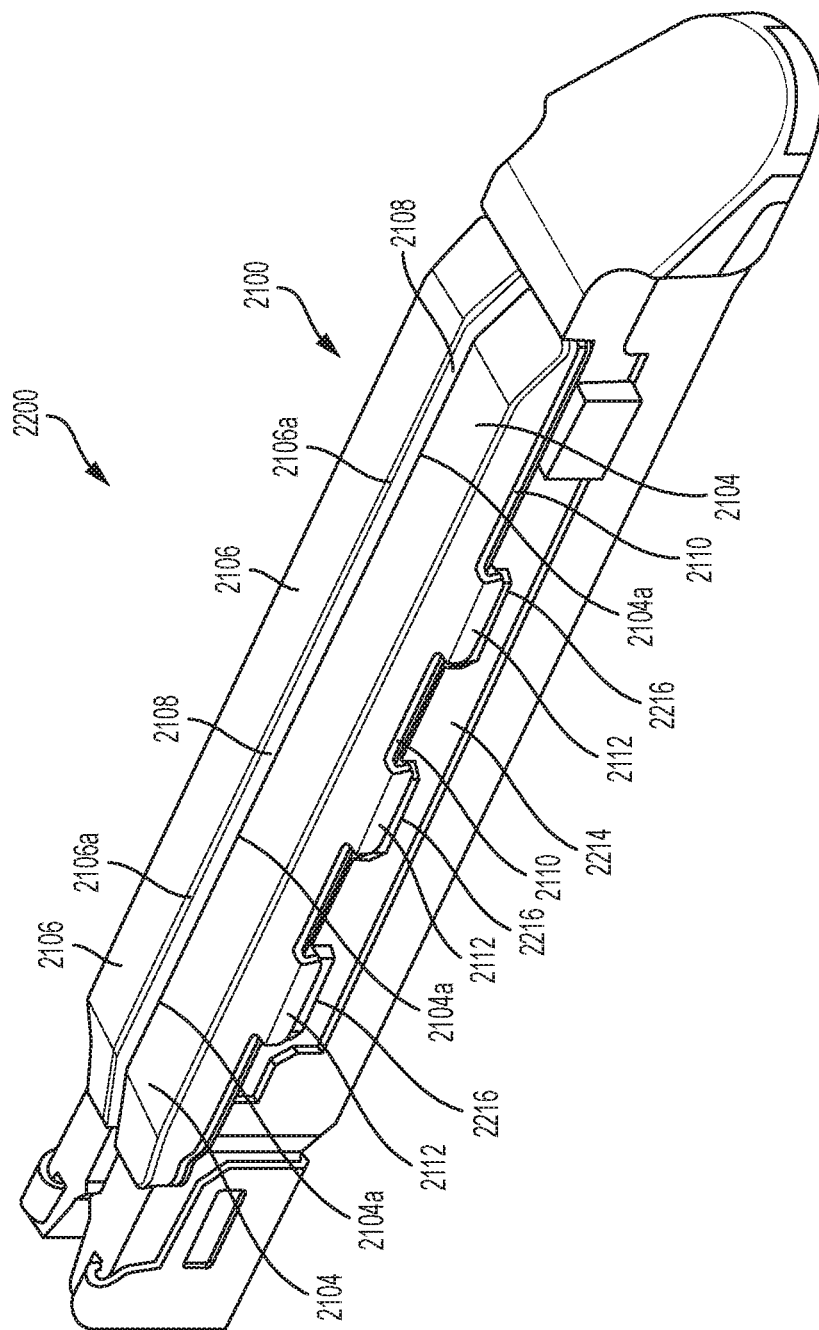
FIG. 21B is an exemplary embodiment of a staple cartridge assembly having the adjunct shown in FIG. 21A attached to a cartridge body.

FIG. 21B illustrates an embodiment of a staple cartridge assembly 2200. Aside from the differences described in detail below, the staple cartridge assembly 2200 can be similar to staple cartridge assembly 600 (FIG. 6) and is therefore not described in detail herein. Further, for purposes of simplicity, certain components of the staple cartridge assembly 2200 are not illustrated in FIG. 21B.

The staple cartridge assembly 2200 includes the adjunct 2100 in FIG. 21A attached to a cartridge body 2214. The adjunct 2100 can be attached to the cartridge body 2214 using any suitable methods, as described in more detail below. In this embodiment, the cartridge body 2214 includes recessed channels 2216 that are configured to receive the flanges 2112 on the adjunct such that the flanges 2112 can engage the side(s) of the cartridge body 2214. In this way, the adjunct 2100 can be more securely attached to the cartridge body, thereby preventing undesired movement of the adjunct 2100 during use.

Figure 22:
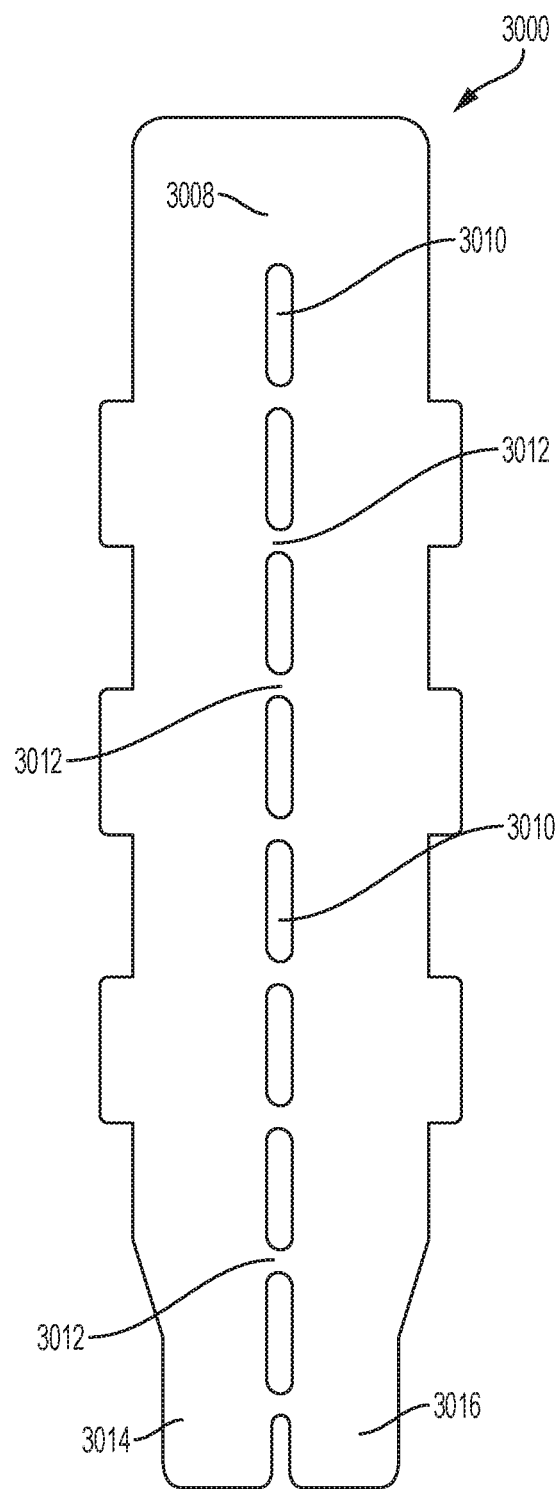
FIG. 22 is an exemplary embodiment of an adjunct having bridging members.

In another embodiment, as shown in FIG. 22, the adjunct 3000 can have a channel 3008 that has one or more openings 3010 extending therethrough (e.g., perforated), thereby creating at least one bridging member 3012. As such, the first and second portions 3014, 3016 of the adjunct 3000 are selectively connected by the at least one bridging member 3012. In use, when the cutting member is initially fired and travels along the adjunct 3000, the cutting member cuts through the at least one bridging member 3012, thereby separating the first and second portions 3014, 3016, and thus separating the adjunct 3000 into two separate pieces.

In some embodiments, the cartridge body, like cartridge body 2214 in FIG. 21B, and the adjunct, like adjunct 3000 in FIG. 22, can include complementary reinforcement features that can be configured to prevent tearing of the adjunct outside of the channel when the cutting element moves through the adjunct 3000. For example, the reinforcement features of the cartridge body can be cylindrical recessed openings positioned proximate to the slot within the cartridge body and the reinforcement features of the adjunct can be cylindrical protrusions positioned within the first and second portions of the adjunct proximate to the at least one bridging member. In this way, when the adjunct is placed atop the cartridge body, these cylindrical protrusions of the adjunct will extend into these recessed openings of the cartridge body. It is also contemplated that these protrusions and recessed openings can take the form of other various shapes.

The scaffolds can be applied to a cartridge body to form a staple cartridge assembly using any suitable method. For example, in some embodiments, the method can include attaching a compressible, bioabsorbable adjunct to a cartridge body of a surgical stapler. In one embodiment, as discussed above, the attachment of the adjunct to the cartridge body can include placing a cartridge-contacting surface of the adjunct against a surface of the cartridge body so as to insert flanges of the adjunct into recessed channels of the cartridge body. In another embodiment, the method can also include coating a surface of the cartridge body with an adhesive prior to attaching the adjunct thereto.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A stapling assembly for use with a surgical stapler, comprising:
   a body having a plurality of staples disposed therein, the plurality of staples being configured to be deployed into tissue, and the body having a first end, a second end, and a longitudinal axis extending therebetween; and
   a three-dimensional compressible adjunct configured to be releasably retained on the body such that the adjunct can be attached to tissue by the plurality of staples in the body, the adjunct having a first component formed from a first matrix comprising at least one fused bioabsorbable polymer, and a second component formed from a second matrix comprising at least one fused bioabsorbable polymer that differs from the at least one fused bioabsorbable polymer of the first matrix, the first and second components being coupled to one another to form a composite structure, wherein the first component includes a plurality of struts that form a plurality of arrays, each array having a repeating X pattern that lies within a single common plane.

2. The stapling assembly of claim 1, wherein the first component has a degradation rate that differs from a degradation rate of the second component.

3. The stapling assembly of claim 1, wherein the first component is configured to bend to allow the adjunct to compress toward the body.

4. The stapling assembly of claim 1, wherein the second component is more flexible than the first component.

5. The stapling assembly of claim 1, wherein at least one of the first matrix and the second matrix includes at least two different fused bioabsorbable polymers.

6. The stapling assembly of claim 1, wherein the first matrix includes at least two fused bioabsorbable polymers, and wherein a first of the at least two fused bioabsorbable polymers has a degradation rate that differs from a degradation rate of a second of the at least two fused bioabsorbable polymers.

7. The stapling assembly of claim 1, wherein the first component has a first color and the second component has a second color that differs from the first color.

8. The stapling assembly of claim 1, wherein the second component comprises a plurality of rods that interconnect the plurality of struts, and wherein each rod extends laterally relative to the longitudinal axis of the body.

9. The stapling assembly of claim 1, wherein the at least one fused bioabsorbable polymer of the first component is polyglactin or polydioxanone.

10. The stapling assembly of claim 1, wherein the at least one fused bioabsorbable polymer of the second component is a polycaprolactone copolymer.

11. The stapling assembly of claim 1, wherein at least one of the first component and the second component is at least partially coated with a bioabsorbable polymer that is different than the at least one fused bioabsorbable polymer of the first matrix and of the second matrix.

12. The stapling assembly of claim 11, wherein the bioabsorbable polymer has a slower degradation rate than a degradation rate of the at least one fused bioabsorbable polymer of the first matrix and of the second matrix.

13. The stapling assembly of claim 1, wherein the adjunct is configured to apply a stress of at least about 3 $g/mm^2$ to the tissue stapled thereto for at least 3 days when the adjunct is in a tissue deployed state.

14. A stapling assembly for use with a surgical stapler, comprising:
   a body having a plurality of staples disposed therein, the plurality of staples being configured to be deployed into tissue; and
   a three-dimensional compressible adjunct configured to be releasably retained on the body such that the adjunct can be attached to tissue by the plurality of staples in the body, wherein the adjunct is a fused structure having a plurality of repeating unit cells that are interconnected at first nodes, each repeating unit cell having a plurality of struts that are interconnected at second nodes, the plurality of struts being formed of a first fused matrix, and the first and second nodes being formed of a second fused matrix that is more flexible than the first fused matrix.

15. The stapling assembly of claim 14, wherein the first fused matrix has a degradation rate that differs from a degradation rate of the second fused matrix.

16. The stapling assembly of claim 14, wherein at least one of the first fused matrix and the second fused matrix includes at least two different fused bioabsorbable polymers.

17. The stapling assembly of claim 14, wherein the first fused matrix comprises at least two fused bioabsorbable polymers, and wherein a first of the at least two fused bioabsorbable polymers has a degradation rate that differs from a degradation rate of a second of the at least two fused bioabsorbable polymers.

18. The stapling assembly of claim 14, wherein the first fused matrix comprises at least one fused bioabsorbable polymer, and wherein the at least one fused bioabsorbable polymer is polyglactin or polydioxanone.

19. The stapling assembly of claim 14, wherein the second fused matrix comprises at least one fused bioabsorbable polymer, and wherein the at least one fused bioabsorbable polymer is a polycaprolactone copolymer.

20. The stapling assembly of claim 14, wherein the adjunct is configured to apply a stress of at least about 3 $g/mm^2$ to the tissue stapled thereto for at least 3 days when the adjunct is in a tissue deployed state.

* * * * *